United States Patent [19]

Thominet et al.

[11] Patent Number: 4,673,686

[45] Date of Patent: Jun. 16, 1987

[54] NEW SUBSTITUTED HETEROCYCLIC BENZAMIDES, METHODS OF PREPARING THEM AND THEIR APPLICATION AS BEHAVIOR MODIFIERS

[75] Inventors: Michel Thominet, Paris; Jacques Acher, Itteville; Jean-Claude Monier, Lardy, all of France

[73] Assignee: Societe D'Etudes Scientifiques et Industrielle de L'Ile de France, Paris, France

[21] Appl. No.: 769,796

[22] Filed: Aug. 26, 1985

Related U.S. Application Data

[60] Continuation of Ser. No. 620,005, Jun. 12, 1984, abandoned, which is a division of Ser. No. 395,994, Jul. 7, 1982, abandoned, which is a continuation of Ser. No. 505,191, Jan. 22, 1979, abandoned.

[30] Foreign Application Priority Data

Jan. 20, 1978 [FR] France .................. 78 10633
Nov. 7, 1978 [FR] France .................. 78 31458

[51] Int. Cl.$^4$ .............. A61K 31/41; A61K 31/40; C07D 249/18; C07D 207/09
[52] U.S. Cl. ................. 514/359; 548/259; 548/567; 514/428; 514/872
[58] Field of Search ............ 548/567, 259; 514/359, 514/428, 872

[56] References Cited

U.S. PATENT DOCUMENTS

| | | | |
|---|---|---|---|
| 3,342,826 | 9/1967 | Miller et al. | 424/274 |
| 3,577,440 | 5/1971 | Lunsford et al. | 424/274 |
| 3,839,330 | 10/1974 | Thominet | 548/259 |
| 3,862,139 | 1/1975 | Podisva et al. | 548/567 |
| 3,959,477 | 5/1976 | Thominet | 424/272 |
| 4,029,673 | 6/1977 | Bulteau et al. | 548/567 |
| 4,039,672 | 8/1977 | Bulteau et al. | 548/253 |
| 4,048,321 | 9/1977 | Berigi et al. | 514/872 |
| 4,089,960 | 5/1978 | Gosteli et al. | 514/872 |
| 4,097,487 | 6/1978 | Murakami et al. | 548/567 |
| 4,158,060 | 6/1979 | Kaplan et al. | 548/567 |
| 4,172,143 | 10/1979 | Kaplan et al. | 548/567 |
| 4,197,243 | 4/1980 | Murakami et al. | 548/567 |
| 4,279,822 | 7/1981 | Cale et al. | 548/557 |
| 4,294,828 | 10/1981 | Thominet et al. | 548/567 |
| 4,330,472 | 5/1982 | Ogata et al. | 548/567 |
| 4,346,089 | 8/1982 | Halley, II et al. | 514/872 |
| 4,350,691 | 9/1982 | Hatley et al. | 514/872 |
| 4,351,770 | 9/1982 | Ogata et al. | 548/567 |
| 4,352,802 | 10/1982 | Blaney | 514/872 |
| 4,431,663 | 2/1984 | Masaru et al. | 514/428 |
| 4,434,170 | 2/1984 | Dosert et al. | 546/112 |

FOREIGN PATENT DOCUMENTS 2097031 7/1970 France .................. 514/428

OTHER PUBLICATIONS

Derwent Abst. 83-772181/39; EPO 0088849-9/83, Choay SA (C83-092332).
Derwent Abst. C83-000349) EPO 0067615, 12/82, Beecham Group.

Primary Examiner—Glennon H. Hollrah
Assistant Examiner—D. L. Dinner
Attorney, Agent, or Firm—Fitzpatrick, Cella, Harper & Scinto

[57] ABSTRACT

There are provided new substituted heterocyclic benzamides and derivatives thereof which provide modifications on the central nervous system.

7 Claims, No Drawings

NEW SUBSTITUTED HETEROCYCLIC BENZAMIDES, METHODS OF PREPARING THEM AND THEIR APPLICATION AS BEHAVIOR MODIFIERS

This application is a continuation of application Ser. No. 620,005 filed June 12, 1984, abandoned. which is a division of application Ser. No. 395,994, filed July 7, 1982 now abandoned, which is a continuation of parent application Ser. No. 005,191, filed Jan. 22, 1979, now abandoned.

The compounds of the present invention are novel o-anisamides and derivatives, having strong properties as modifiers of the central nervous system as show by their anti-apomorphine power.

The invention relates to new substituted heterocyclic benzamides of the general formula:

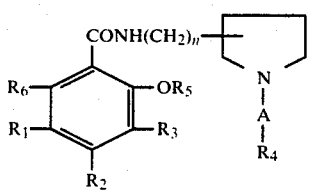

(I)

in which:

$R_4$ is a cycloalkyl, cycloalkenyl, bicycloalkyl or tricycloalkyl group.

A is a single bond or a saturated or unsaturated hydrocarbon chain with 1 to 3 carbon atoms.

n is equal to 0, 1, 2 or 3.

$R_5$ is a hydrogen atom, an alkyl group with 1 to 3 carbon atoms or an alkenyl or alkynyl group.

$R_1$, $R_2$, $R_3$, $R_6$ are hydrogen or halogen atoms, alkyl, alkoxy, amino, acetamino, sulphamoyl, alkylsulphamoyl, dialkylsulphamoyl, alkylsulphonyl or alkylsulphinyl groups or are bonded together to form an azimido group.

with the following provisos:

when $R_4$ is a cycloalkyl group, $R_5$ a hydrogen atom or an alkyl group, A a single bond and n equal to 0, at least one of the substituents $R_1$, $R_2$, $R_3$, $R_6$ is an alkylsulphonyl or alkylsulphinyl group or two of these substituents are bonded together to form an azimido group.

when $R_4$ is a cycloalkyl group, $R_5$ a methyl group and A an alkylene group with one to three carbon atoms, n is equal to 1 and the amide chain is bonded at the 2 position of the pyrrolidine, $R_1$ can be a halogen atom or a sulphamoyl, alkylsulphamoyl, dialkylsulphamoyl or alkylsulphonyl group only in cases where $R_2$, $R_3$, $R_6$ are not simultaneously hydrogen atoms.

The invention also concerns salts of addition to pharmacologically acceptable acids, quaternary ammonium salts, oxides and levorotatory and dextrorotatory isomers of the compounds of formula (I).

The compounds of the invention are prepared by reacting an acid of the formula:

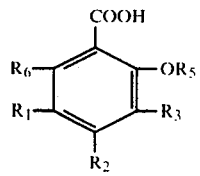

(II)

wherein $R_1$, $R_2$, $R_3$, $R_5$, $R_6$ are defined as above, or one of its reactive derivatives such as its acid halide, alkyl ester, reactive ester such as its methoxy methyl ester or cyanomethyl ester, aromatic ester, N-hydroximide ester, symmetrical anhydride or mixed anhydride, formed e.g. from a carbonic acid ester or a haloformic ester, or its azide, hydrazide, azolide, acid isothiocyanate, trichloroacetophone, or triphenylphosphine derivative, with an amine of the formula:

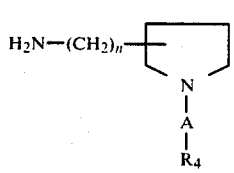

(III)

wherein A, $R_4$ and n are defined as above, or one of its reactive derivatives such as the derivative obtained by reacting the amine with a phosphorus chloride, the phosphorus oxychloride, a dialkyl, diaryl or orthophenylenechlorophosphite, an alkyl or aryldichlorophosphite, an isothiocyanate of the amine, a sulphamide or a substituted urea.

The invention is not limited to derivatives of the acid and amine mentioned above.

The amidifying reaction may be carried out in situ or when the intermediate derivative has been isolated.

It is also possible to react the free acid and the free amine in the presence of a condensing agent such as silicon tetrachloride, trichlorophenylsilane, phosphoric anhydride, a carbodiimide or an alkoxyacetylene.

The formula (I) compounds may equally be prepared by reacting the formula (II) acid or one of its reactive derivatives defined as above, with a dihaloalkylamine of the formula:

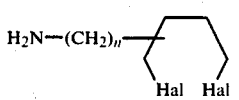

(IV)

wherein n is defined as above and the halogen is a chlorine, bromine or iodine atom, then by reacting the compound obtained, of the formula:

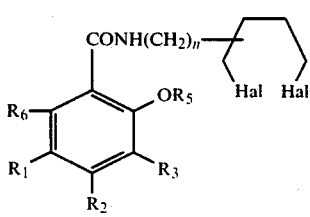

(V)

with an amine of the formula:

$H_2N-A-R_4$ (VI)

wherein $R_4$ and A are defined as above.

The methods of preparing the compounds according to the invention are set out in the following diagram:

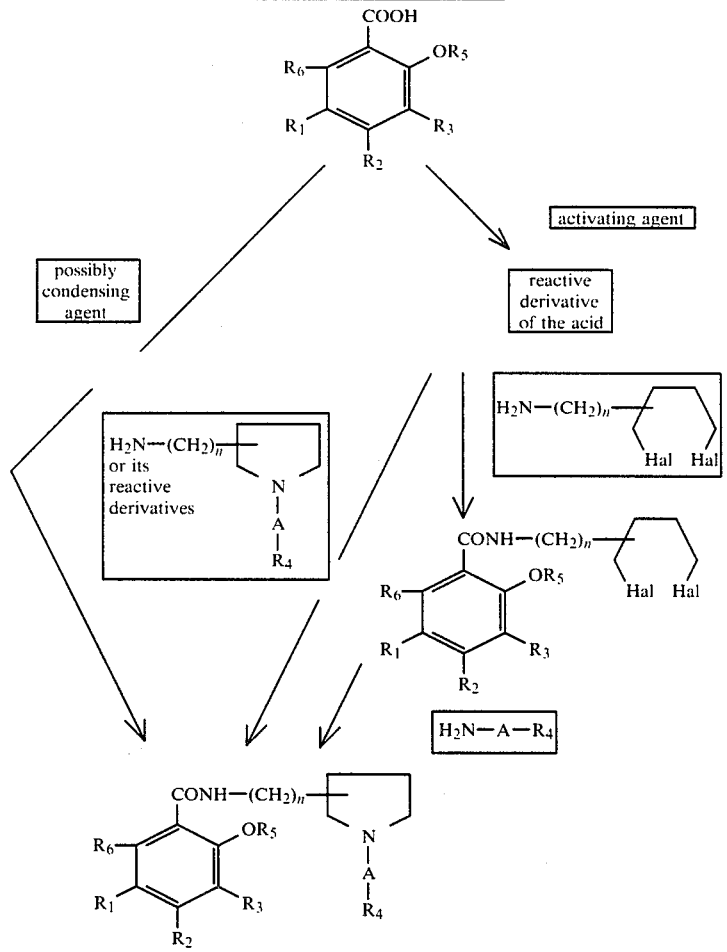

The amidifying reactions may take place with or without a solvent.

Some examples of the systems used as solvents, which are inert relative to the amidifying reaction, are alcohols, polyols, ketones, benzene, toluene, dioxan, chloroform and diethyleneglycoldimethyl ether. It is also possible to take an excess of the amine used as raw material as the solvent. It may be preferable to heat the reaction mixture during amidification, e.g. to the boiling point of the above mentioned solvents.

The compound obtained by the method of the invention may, if necessary, react with pharmaceutically acceptable inorganic or organic acids such as hydrochloric, hydrobromic, sulphuric, phosphoric, oxalic, acetic, tartaric, citric or methane-sulphonic acid, to give acid addition salts.

It may equally react, if necessary, with alkyl sulphates or halides to give quaternary ammonium salts.

It may also be oxidised in known manner, e.g. with hydrogen peroxide and manganese dioxide, to give the corresponding N-oxide.

Some examples will now be given to illustrate the technical features of the invention. It should be understood that the invention is not limited to these embodiments nor to the purposes to which they can be applied.

EXAMPLE 1

N-(1-cyclohexyl-2-pyrrolidinyl-methyl)-2-methoxy-4-amino-5-chlorobenzamide 240 g of 2-methoxy-4-acetamino-5-chloro-benzoic acid (0.985 mole), 960 ml of acetone and 99.5 g of triethylamine (0.985 mole) are placed in a 3 liter flask fitted with an agitator, a thermometer and a dropping funnel. The acid dissolves almost entirely. The reaction medium is cooled to 0° C.: the triethylamine salt of the acid crystallises.

107 g of ethyl chloroformate (0.985 mole) is added to the suspension, drop by drop, and the temperature is kept between 0° and +5° C. This takes about 1 hour 30. Agitation is continued for a further 30 minutes, then 188 g of 1-cyclohexyl-2-amino-methyl pyrrolidine is added drop by drop over about 1 hour while the temperature is kept between +10° and +15° C. When all the pyrrolidine has been added, agitation is continued for a further ½ hour at +10° C. then for 1 hour at room temperature. The base crystallises. It is drained and washed with acetone. The precipitate is immediately dissolved in 1 liter of water in order to dissolve the triethylamine hydrochloride; it is drained, washed with water until the Cl− ions have been eliminated, and dried at 50°. Weight obtained 262 g.

The acetone mother liquor is evaporated under vacuum to constant weight. Weight 161 g for 139 g theory.

790 ml of 2.5N alcoholic potash (2×0.985 mole) and the 423 g of crude acetylaced base are placed in a 2 liter flask fitted with a reflux condenser. The mixture is heated to reflux for 2 hours. The solution is filtered with charcoal then diluted with 6 liters of water. The deacetylated base is precipitated in liquid form then crystallises after standing overnight. It is drained, washed with water and dried in air then at 40° C. 324 g of the product is obtained, melting at 115°–116° C.

The 324 g of base is dissolved hot in 625 ml of aceto-nitrile. The turbid solution is filtered boiling, through charcoal, then cooled. The base recrystallises and is drained, washed with aceto-nitrile, then dried. 290 g of a beige substance is obtained. The base obtained is re-crystallised a second time in 580 ml of aceto-nitrile with filtration through charcoal. 271 g of the product, which is still beige, is obtained.

The 271 g of base is dissolved in 2.7 liters of water and the necessary hydrochloric acid. The solution is filtered with charcoal, then the base is precipitated by adding 20% ammonia. It is liquid at first and crystallises after 24 hours.

The crystals are drained, washed with water and dried in an oven at 40° C. 256 g is obtained and re-crystallised in 510 ml of acetonitrile. The boiling solution is filtered. After cooling, the re-crystallised base is drained, washed with acetonitrile and dried in air, then at 50° C.

235 g of N-(1-cyclohexyl-2-pyrrolidinylmethyl)-2-methoxy-4-amino-5-chlorobenzamide is obtained, melting at 123°–124° C. Yield 65%.

EXAMPLE 2

N-(1-cyclopentyl-2-pyrrolidinylmethyl)-2-methoxy-4-chloro-5-ethyl sulphonylbenzamide 2-methoxy-4-chloro-5-chlorosulphonylbenzoic acid 4 liters of chlorosulphonic acid is placed in a 3-necked 6liter flask, fitted with an agitator and a thermometer, and cooled to +15° C.

563 g of 2-methoxy-4-chloro benzoic acid (3.01 moles) is added in fractions and the temperature is allowed to develop. The benzoic acid takes 20 min. to add, and the temperature reaches 50° C. The mixture is immediately heated to 80° C., then the temperature is allowed to drop to 40° C.

The reaction mixture is poured over 30 kg of ice, then the precipitate is drained, washed with water and dried at 50° C. 764 g (89%) of product is obtained, melting at 179° C.

2-methoxy-4-chloro-5-ethylsulphonyl benzoic acid.

3 liters of water, 740 g of sodium sulphite and 535 g of sodium bicarbonate are placed in a 3-necked 10 liter flask fitted with an agitator, a thermometer and a condenser. The mixture is heated to 70° C. and 903 g of 2-methoxy-4-chloro-5-chlorosulphonyl benzoic acid is added in fractions while the temperature is kept between 70° and 75° C.

The temperature is kept at 75° C. for 3 hours then reduced to 25° C. 750 ml of ethanol is introduced, then 950 g of sodium bicarbonate is added with care. Finally 1,270 g of ethyl iodide and 2,250 ml of ethanol are added. The medium is heated gently to reflux (35° C.) and the reflux is maintained for 17 hours (82° C.).

3 liters of a mixture of alcohol, water and ethyl iodide is distilled under vacuum, then 3 liters of water is added to the concentrate. It is acidified to pH 1 with about 1,100 ml of hydrochloric acid and cooled to about 10° C., after which it is drained and washed with 3 liters of water. The product is dissolved in 3 liters of water containing 300 g of sodium bicarbonate. It is agitated for 2 hours, then the insoluble part is filtered off. 100 g of vegetable black is added to the filtrate, then it is agitated and the black is filtered off. The product is precipitated by acidifying it with about 300 ml of hydrochloric acid at 1.18 density. The product is drained, washed several times with water and dried in an oven at 60° C.

550 g (62.5%) of acid is obtained, melting at 180° C.

2-methoxy-4-chloro-5-ethylsulphonyl benzoyl chloride 139 g of 2-methoxy-4-chloro-5-ethylsulphonyl benzoic acid, 200 ml of thionyl chloride and 0.5 ml of dimethylformamide are placed in a flask fitted with an agitator, a thermometer and a condenser.

The mixture is heated to reflux, left to stand, then the solution is evaporated dry.

The residue is treated with 200 ml of toluene, then the crystals are washed with toluene and dried in a vacuum desiccator.

117 g of 2-methoxy-4-chloro-5-ethylsulphonyl benzoyl chloride is obtained (M.P.=115°–117° C., yield=79%.

N-(1-cyclopentyl-2-pyrrolidinylmethyl)-2-methoxy-4-chloro-5-ethyl sulphonylbenzamide 54 g of 1-cyclopentyl-2-aminomethyl-pyrrolidine (0.32 mole) and 300 ml of methyl-ethyl-ketone are placed in a 1 liter flask fitted with an agitator and a thermometer. The solution is cooled to +10° C., then 89 g of 2-methoxy-4-chloro-5-ethylsulphonyl benzoyl chloride (0.30 mole) is added in stages. The reaction medium is agitated for 2 hours at room temperature then left to stand overnight. The crystals are filtered, washed three times with 100 ml of methyl-ethyl-ketone, then dried in an oven at 60° C.

85 g of product is obtained, melting at 165°–170° C.

The hydrochloride is re-crystallised in 400 ml of methyl-ethyl-ketone. The product is filtered, washed with a little solvent and dried in an oven at 50° C.

69 g (49.5%) of product is obtained, which melts and decomposes at 160° C.

EXAMPLE 3

N-(1-cyclopropylmethyl-2-pyrrolidinylmethyl)-2,3-dimethoxy-5-sulphamoyl benzamide 2,3-dimethoxy-5-sulphamoyl benzoyl chloride 419 g (1.6 mole) of 2,3-dimethoxy-5-sulphamoyl benzoic acid and 1,351 g (11.35 moles) of thionyl chloride are placed in a 2 liter flask fitted with an agitator, a thermometer and a condenser connected to a soda bubbler. The mixture is brought to reflux for 1 hour, after which the excess thionyl chloride is expelled under vacuum. The residue is dissolved in 1,000 ml of hexane, filtered, washed twice with 500 ml of petroleum ether and dried in a desiccator under vacuum. 424 g (yield 94.8%) of 2,3-dimethoxy-5-sulphamoyl benzoyl chloride is obtained, with a melting point of 153° C.

N-(1-cyclopropyl-methyl-2-pyrrolidinyl-methyl)-2,3-dimethoxy-5-sulphamoyl benzamide 20 g (0.13 moles) of 1-cyclopropyl-methyl-2-aminomethyl-pyrrolidine and 150 ml of methyl-ethyl-ketone are placed in a 500 ml flask fitted with an agitator, a thermometer and a condenser. 36.3 g (0.13 mole) of 2,3-dimethoxy-5-sulphamoyl benzoyl chloride is also introduced in stages and the temperature is kept between 15° and 20° C. The thick paste obtained is diluted with 170 ml of water and reacted for 1 hour at ambient temperature. It is then evaporated dry and the residue is dissolved in 200 ml of water and made alkaline with an excess of ammonia. The base is precipitated and crystallises slowly. The crystals are filtered, washed with water and dried in an oven at 50° C. 50 g (yield 97%) of N-(1-cyclopropyl-methyl-2-pyrrolidinyl-methyl) 2,3-dimethoxy-5-sulphamoyl benzamide is obtained. This is re-crystallised three times in butyl acetate, and 26 g (50.5%) of crystals is obtained. The crystals are dissolved in normal hydrochloric acid, filtered, made alkaline with normal soda and re-filtered. They are washed with water until the Cl− ions have completely disappeared and dried in an oven (50° C.), to give 24 g(46.6%) of crystals which melt at 136° C. (they are insoluble in water).

| Analyses | Calculated | Found |
|---|---|---|
| S% | 8.06 | 8.13 |

EXAMPLE 4

N-(1-cyclopropyl-methyl-2-pyrrolidinyl-methyl)-2-methoxy-4-amino-5-ethylsulphonyl-benzamide 2-methoxy-4-amino-5-ethylthiobenzoic acid 159 g of 2-methoxy-4-amino-5-mercaptobenzoic acid, 355 cm$^3$ of water and 160 cm$^3$ of soda lye are placed in a flask fitted with a condenser. The mixture is heated till the solids have dissolved, then 123 g of ethyl sulphate is added. The mixture is heated to reflux, treated with 10 cm$^3$ of 30% of soda lye, then heated to reflux for 1 hour. It is cooled, 800 cm$^3$ of water is added and the solution is filtered. The precipitate, obtained by adding 100 cm$^3$ of concentrated hydrochloric acid in the presence of ether, is drained, washed with water and dried.

162 g of 2-methoxy-4-amino-5-ethylthio benzoic acid is obtained (yield 88%).

2-methoxy-4-amino-5-ethylsulphonyl benzoic acid 123 g of 2-methoxy-4-amino-5-ethyl thiobenzoic acid is dissolved hot in 542 cm$^3$ of acetic acid. The solution obtained is cooled to 35° C., then 185 cm$^3$ of 131 vol. hydrogen peroxide is added in small quantities and the temperature is raised to 80° C.

The temperature is lowered to 40° C. and the mixture is kept at that temperature for a few hours, then cooled to 10° C.

The precipitate formed is drained, washed with acetic acid and dried, then dissolved in 600 cm$^3$ of water and 100 cm$^3$ of 20% ammonia.

The precipitate formed by adding 70 cm$^3$ of concentrated hydrochloric acid is cooled, drained, washed with water and dried.

61.5 g of hydrated 2-methoxy-4-amino-5-ethylsulphonyl benzoic acid is obtained (yield=42%—M.P.=95°-100° C.).

N-(1-cyclopropyl-methyl-2-pyrrolidinyl-methyl)-2-methoxy-4-amino-5-ethylsulphonyl-benzamide 31.3 g (0.31 mole) of triethylamine, 400 ml of tetrahydrofuran and 80.3 g (0.31 mole) of 2-methoxy-4-amino-5-ethylsulphonyl benzoic acid are placed in a 1 liter flask fitted with an agitator, a thermometer, a condenser and a dropping funnel. A rubbery precipitate is formed which gradually crumbles. After 30 minutes at room temperature it is cooled to 0° C. and 33.6 g (0.31 mole) of ethyl chloroformate is added drop by drop.

This is kept under agitation for 1 hour between 0° and 5° C. and 62 g (0.40 mole) of 1-(cyclopropylmethyl)-2-amino-methyl-pyrrolidine is added drop by drop while the temperature is kept at the same level. A thick precipitate is formed. The reaction medium is agitated for a further 2 hours at room temperature then left to stand overnight. The crystals obtained are filtered, washed twice with 100 ml of tetrahydrofuran and dried in an oven at 50° C. 137 g of product is obtained and is dissolved with boiling water. After filtering and drying, 91 g (74.3%) of crystals is obtained; these are re-crystallised in 600 ml of 90% alcohol. They are filtered, washed twice with 50 ml of alcohol and dried in an oven at 40° C. 81.5 g (yield 66.5%) of N-(1-cyclopropyl-methyl-2-pyrrolidinyl-methyl)-2-methoxy-4-amino-5-ethylsulphonyl benzamide is obtained, melting at 181° C.

| Analyses | Calculated | Found |
|---|---|---|
| S% | 8.11 | 8.06 |

EXAMPLE 5

N-(1-cyclopropyl-2-pyrrolidinylmethyl)-2-methoxy-5-sulphamoyl benzamide 2,5-dichloropentylamine hydrochloride 1,010 g (10 moles) of tetrahydrofurfurylamine is placed in a 10 liter flask fitted with a mechanical agitator, a condenser connected to a bubbler which contains sulphuric acid, and a gas inlet tube, and a stream of hydrochloric acid, previously dried by bubbling through sulphuric acid, is passed through while the temperature is kept at 100°–110° C.

The reaction is exothermic at the beginning. When the flow of gas at the inlet and the outlet is identical, the tube is removed, the reaction medium cooled to 60° C. and 4 liters of chloroform is stirred in. The temperature is lowered to 30° C. and 1,500 ml of thionyl chloride is added drop by drop. After 2 hours at reflux the 2,5-dichloropentylamine hydrochloride is precipitated. It is filtered, washed with chloroform and dried at 70° C. 1,512 g (yield 78.5%) of product is obtained, which melts at 160° C.

2-methoxy-5-sulphamoyl-benzoyl chloride 23.1 g (0.1 mole) of 2-methoxy-5-sulphamoyl-benzoic acid in 400 ml of dichloroethane and 1 ml of dimethylformamide is placed in a 1 liter flask fitted with a mechanical agitator, a dropping funnel and a condenser. 11 ml (0.15 mole) of thionyl chloride is stirred in rapidly and the medium is heated to reflux until the solids are completely dissolved.

After cooling to 50° C. the medium is filtered, and the chloride obtained is dried in a vacuum desiccator.

20.2 g of 2-methoxy-5-sulphamoyl-benzoyl chloride is obtained; this melts at 167° C. (with decomposition).

| Analyses | Calculated | Found |
|---|---|---|
| Cl % | 14.22% | 14.6% |

N-(2,5-dichloropentyl)-2-methoxy-5-sulphamoyl-benzamide 77.5 g (0.4 mole) of 2,5-dichloropentylamine hydrochloride dissolved in 500 ml of dichlorethane is placed in a 2 liter flask fitted with an agitator, a thermometer, a condenser and dropping funnel, followed by 112 ml of triethylamine. A solution of 100 g (0.4 mole) of 2-methoxy-5-sulphamoyl-benzoyle chloride in 1 liter of methyl ethyl ketone is then poured in, while the temperature is kept at 20° C.

After a reaction lasting 1 hour the precipitate of triethylamine hydrochloride is filtered and the filtrate is evaporated dry under vacuum. The precipitate is dissolved in 1 liter of water. Crystals are left, which are filtered and washed twice with 100 ml of isopropanol. They are added to the residue of the evaporated filtrate, and the solid is re-crystallised in 1,600 ml of isopropanol. The crystals are filtered, washed with isopropanol and dried in an oven at 40° C. 101 g (68.4%) of N-(2,5-dichloropentyl)-2-methoxy-5-sulphamoyl-benzamide is collected, melting at 148° C.

N-(1-cyclopropyl-2-pyrrolidinylmethyl)-2-methoxy-5-sulphamoyl-benzamide 36.9 g (0.1 mole) of N-(2,5-dichloropentyl)-2-methoxy-5-sulphamoyl-benzamide and 57 g of cyclopropylamine are placed in 250 ml bottle. They are brought to reflux for 6 hours, left to stand for 1 night then brought back to reflux for 5 hours. The suspension obtained is poured into 300 ml of water and 50 g of ice. The white precipitate is washed with water and dried in an oven at 60° C. It melts at 163° C. and weighs 29.5 g (83.6%). It is dissolved in 2 liters of acetonitrile and filtered in the presence of carbon black. The filtrate is left to crystallise. The crystals obtained are filtered, washed with acetonitrile and dried at 40° C. 67 g (yield 74.9%) of N-(1-cyclopropyl-2-pyrrolidinylmethyl)-2-methoxy-5-sulphamoylbenzamide is collected, melting at 180° C.

| Analyses | Calculated | Found |
|---|---|---|
| N % | 11.89 | 11.74 |
| S % | 9.07 | 9.19 |

EXAMPLE 6

N-(1-cyclopropyl-2-pyrrolidylmethyl)-2-methoxy-4-amino-5-dimethyl-sulphamoylbenzamide 2-methoxy-4-amino-5-dimmethylsulphamoyl benzoic acid In 4 liter flask fitted with a reflux condenser, 300 g of 2-methoxy-4-amino-5-sulphamoyl benzoic acid (1.22 mole) is dissolved in 735 ml of water and 365 ml of soda lye ($3 \times 1.22$ mole). 308 g of methyl sulphate ($2 \times 1.22$ mole) is added and the medium is heated to reflux. It is cooled and methylation is recommenced, once with 122 ml of soda lye and 154 g of methyl sulphate, and once with 61 ml of soda lye and 77 g of methyl sulphate. The reaction medium is heated to reflux for about ¼ hour each time. When the reaction is over 22 ml of soda lye is added and the medium is heated to reflux for ½ hour. The solution is cooled then filtered with charcoal. The acid is precipitated by adding 140 ml of concentrated hydrochloric acid. It is drained, washed with water and dried at 50° C. 304.5 g of product is obtained; this melts to about 150° C., then re-crystallises and melts at 176°–178° C.

The product is re-crystallised in 609 ml of acetic acid, drained, washed with 60 ml of acetic acid then with water, and dried at 50° C. 239 g (71%) of white product is obtained, melting at 187°–189° C.

N-(1-cyclopropyl-2-pyrrolidylmethyl)-2-methoxy-4-amino-5-dimethylsulphamoyl benzamide ≃→

68.5 g of 2-methoxy-4-amino-5-dimethylsulphamoyl benzoic acid (0.25 mole), 740 ml of water and 25.4 g of triethylamine (0.25 mole) are placed in a 2 liter flask fitted with an agitator, a thermometer, a condenser and a dropping funnel. The solution is cooled to about 0° C, and 34.1 g of isobutyl chloroformate (0.25 mole) is poured in drop by drop. The mixture is reacted for 40 minutes at room temperature then cooled, and 42 g of 1-cyclopropyl-2-aminomethylpyrrolidine is added drop by drop, while the temperature is kept between 0° and +5° C. The medium is reacted for 3 hours at room temperature, then the solution is evaporated dry under vacuum. The residue is dissolved in 250 ml of water and 50 ml of hydrochloric acid. The solution is extracted twice with 125 ml of methylene chloride, which is eliminated. The aqueous phase is made alkaline with 70 ml of soda lye.

An oil is precipitated. It crystallises slowly. The crystals are drained, washed with water and dried in an oven at 50° C.

79 g of product is obtained and is re-crystallised in 1,975 ml of ethyl acetate. 38.2 g of amide is obtained, melting at 170° C.

EXAMPLE 7

N-(1-cyclohexyl-2-pyrrolidylmethyl)-2-methoxy-4,5-azimido benzamide 117 g of 5-carbomethoxy-6-methoxy-benzotriazol (0.565 mole), 52 ml of water and 154 g of 1-cyclohexyl-2-aminomethyl-pyrrolidine (0.565 mole + 50% excess) are placed in a 500 ml flask fitted with a reflux condenser. The suspension is heated in a water bath and dissolves rapidly. Heating is continued for 8 hours 30. A sample which is then taken is entirely soluble in dilute acids.

The solution is diluted with 500 ml of water; the base crystallises rapidly. It is drained, washed with water and dried in an oven at 50° C. 143 g of product is obtained; it melts, but not in a clear cut way, at 115°–118° C.

140 g of base is suspended in 450 ml of water. 33 ml of hydrochloric acid (density 1.18) is added. The hydrochloride forms immediately. It is brought to the boil, and the solution obtained is filtered, then cooled. The hydrochloride crystallises in a thick mass, which is drained, washed with 50 ml of ice water and dried. Draining takes a long time and the product retains a great deal of water. 144 g of product is obtained (melting point 153°–155° C.). The 144 g of hydrochloride is dissolved in 700 ml of hot water, and the solution is filtered with charcoal and the base precipitated by adding 40 ml of 20% ammonia. It is liquid at first but crystallises rapidly. The crystals are drained, washed with water and dried at 50° C. 126 g of product is obtained; this melts, but not in a clear cut way, at 110° to 115° C.

This base is dissolved in 250 ml of isopropanol and heated. The suspension is cooled, drained, washed with 30 ml of isopropanol and dried in air, then at 50° C.

114 g of N-(1-cyclohexyl-2-pyrrolidylmethyl)-2-methoxy-4,5-azimidobenzamide is obtained, melting at 173°-174° C. Yield=56%.

EXAMPLE 8

N-(1-cyclopropylmethyl-2-pyrrolidylmethyl)-2-methoxy-3-isopropyl-5-sulphamoyl-6-methylbenzamide 2-methoxy-3-isopropyl-6-methylbenzoic acid 262 g of O-thymotic acid (1.35 mole), 270 ml of 40% soda lye and 400 ml of water are placed in a 3 liter flask fitted with an agitator, a thermometer, a condenser and a dropping funnel. The solution is heated to reflux and 255 ml of dimethyl sulphate is added drop by drop. The reflux is maintained for 30 minutes, then 70 ml of soda lye is added and 65 ml of dimethyl sulphate is dripped in. The reaction is allowed to proceed for 15 minutes, the pH is adjusted to 8-9 by adding 20 ml of soda, and the suspension is cooled to about 10° C. It is acidified with 80 ml of hydrochloric acid, and the suspension is extracted 3 times with 200 ml of ether. The organic phase is evaporated dry under vacuum.

The oily residue is added to a solution of 180 g of potash in pellet form in 675 ml of ethanol at 95°. It is heated to reflux for 1 hour and cooled, then the suspension is evaporated and the residue dissolved in water. The liquid is acidified to pH=1 with hydrochloric acid, and the suspension is extracted 3 times with 300 ml of ether. The organic phase is washed with water, dried over magnesium sulphate and filtered, and the solvent is evaporated under vacuum.

The residue is re-crystallised in 250 ml of petroleum ether, drained and washed 3 times with 100 ml of petroleum ether, and the white crystals are dried in an oven at 40° C. b)

217 g (77%) of product is obtained, melting at 68° C.

2-methoxy-3-isopropyl-5-sulphamoyl-6-methylbenzoic acid 1,200 ml of chlorosulphonic acid is placed in a 4 liter flask fitted with an agitator and a thermometer. 250 g of 2-methoxy-3-isopropyl-6-methyl benzoic acid (1.20 moles) is added in stages between 10° and 15° C. The mixture is agitated for 9 hours at room temperature then left to stand, and the solution is poured drop by drop into a 20 liter reactor containing crushed ice. Effective agitation is necessary, and the temperature is always kept below +5° C. by periodically adding ice. Altogether 10 to 11 kg of ice is used.

The precipitate is filtered, washed with water then introduced in stages into 800 ml of 23% ammonia kept between −5° and +5° C.

When the solids have completely dissolved, the solution is left to stand then filtered in the presence of carbon black. The filtrate is acidified with 500 ml of hydrochloric acid (density 1.18). It is crystallised in a refrigerator, filtered and washed with water. The crystals, which are white, are dried in an oven at 50° C. 291 g (84%) of product is obtained, melting at 198° C.

2-methoxy-3-isopropyl-5-sulphamoyl-6-methylbenzoyl chloride 72 g of 2-methoxy-3-isopropyl-5-sulphamoyl-6-methylbenzoic acid (0.25 mole), 250 ml of chloroform, 23 ml of thionyl chloride and 3 drops of dimethylformamide are placed in a 1 liter flask fitted with an agitator and a condenser. The mixture is heated to reflux for 1.5 hours, then 18 ml of thionyl chloride is added and the reflux is continued for 1.5 hours. The solids dissolve completely.

The solution is cooled and evaporated dry under vacuum, then 100 ml of chloroform is added to the residue and evaporation is continued. There is an oily residue.

N-(1-cyclopropylmethyl-2-pyrrolidylmethyl)-2-methoxy-3-isopropyl-5-sulphamoyl-6-methylbenzamide 4.3 g of 1-cyclopropylmethyl-2-aminomethylpyrrolidine (0.028 mole) and 40 ml of methylethyl ketone are placed in 250 ml flask fitted with an agitator, a thermometer and a dropping funnel. The mixture is cooled to about 10° C. and a solution of 7.6 g of 2-methoxy-3-isopropyl-5-sulphamoyl-6-methyl benzoyl chloride (0.025 mole) in 50 ml of methyl-ethyl-ketone is poured in drop by drop. The mixture is reacted for 1 hour at room temperature then evaporated dry under vacuum, and the residue is dissolved in 100 ml of water and 10 ml of hydrochloric acid (density 1.18). The solution is sucked up under vacuum to eliminate the last traces of solvent, an insoluble component is filtered off and the filtrate is made alkaline with 15 ml of ammonia (density=0.91). The precipitate formed is filtered, washed with water and re-crystallised moist in 50 ml of ethyl acetate. 2.5 g (24%) of product is obtained, melting at about 125° C.

EXAMPLE 9

N-(1-cyclopentyl-2-pyrrolidylmethyl)-2-methoxy-3-isopropyl-5-sulphamoyl-6-methyl benzamide 3.4 g of 1-cyclopentyl-2-aminomethylpyrrolidine (0.020 mole) and 40 ml of methyl-ethyl-ketone are placed in a 250 flask fitted with an agitator, a thermometer and a dropping funnel. The mixture is cooled to about +10° C., then a solution of 5.5 g of 2-methoxy-3-isopropyl-5-sulphamoyl-6-methylbenzoyl chloride (0.018 mole) in 40 ml of methyl-ethyl-ketone is poured in drop by drop. The mixture is reacted 1 hour at room temperature, then the solvent is evaporated under vacuum and the residue dissolved in 100 ml of hydrochloric acid (density 1.18). An insoluble rubbery product is filtered off, and the filtrate is made alkaline with 15 ml of ammonia (density 0.91). The precipitate formed is filtered, washed with water then re-crystallised in 30 ml of ethyl acetate. The crystals are filtered, washed with a little solvent and dried in an oven at 50°046732772 C. 1.3 g (17%) of product is obtained, melting at 196° C.

EXAMPLE 10

N-(1-cyclohexylmethyl-2-pyrrolidylmethyl)-2-methoxy-3-isopropyl-5-sulphamoyl-6-methylbenzamide 4.4 g of 1-cyclohexylmethyl-2-aminomethylpyrrolidine (0.22 mole) and 40 ml of methyl-ethyl-ketone are placed in a 250 ml flask fitted with an agitator, a thermometer and a dropping funnel. The mixture is cooled to about 10° C., and a solution of 6.1 g of 2-methoxy-3-isopropyl-5-sulphamoyl-6-methylbenzoyl chloride (0.20 mole) in 40 ml of methyl-ethyl-ketone is added drop by drop. The reaction medium is agitated for 1 hour at room temperature, then the solution is evaporated under vacuum. The residue is dissolved in 100 ml of water and 10 ml of hydrochloric acid (density 1.18). An insoluble viscous product is filtered off. The filtrate is made alkaline with 15 ml of ammonia (density 0.91). An oil is salted out, then crystallises slowly. The crystals are filtered off, washed with water and recrystallised moist in 50 ml of isopropyl ether. 1.4 g of product is obtained.

It is dissolved in 50 ml of water, 1 ml of hydrochloric acid (density 1.18) and 30 ml of acetone. 50 ml of water is added, and the acetone is distilled under vacuum. The remaining aqueous solution is made alkaline with 2 ml of ammonia (density 0.91). The precipitate formed is filtered, washed with water and dried in an oven at 50° C.

1.2 g (13%) of product is obtained, which melts to a viscous consistency at about 90° C. The NMR and IR spectra are compatible with the structure proposed.

EXAMPLE 11

N-(1-norbornyl-2-pyrrolidylmethyl)-2-methoxy-5-methylsulphonyl benzamide 69 g of 2-methoxy-5-methylsulphonylbenzoic acid (0.30 mole), 360 ml of acetone, 120 ml of water and 30.3 g of triethylamine (0.30 mole) are placed in a 1 liter flask fitted with an agitator, thermometer, a condenser and a dropping funnel. The solution is chilled to 0° C., then 40.8 g of isobutyl chloroformate (0.30 mole) is added drop by drop. The mixture is agitated for 30 minutes at room temperature, then chilled to 0° C. again, and 58.2 g of 1-norbornyl-2-aminomethyl pyrrolidine (0.30 mole) is poured in drop by drop. The reaction mixture is agitated for 3 hours at room temperature then evaporated dry. The residue is dissolved in 500 ml of water and 80 ml of hydrochloric acid (density 1.18). The solution is filtered with acticarbone 3S and the filtrate is made alkaline with 120 ml of soda lye. A thick oil is decanted off, washed with 500 ml of water then dissolved hot, at about 60° C., in 90 ml of ethyl acetate. The product crystallises. The crystals are frozen, filtered and washed in water and dried in an oven at 60° C. 72 g of product is obtained (melting point 125° C.). This is re-crystallised in 150 ml of isopropanol to give 62 g (51%) of amide melting at 132° C.

EXAMPLE 12

N-(1-(-2'-norbornyl)-2-pyrrolidyl)methyl)-2-methoxy-4-amino-5-ethyl sulphonyl-benzamide 26 g of 2-methoxy-4-amino-5-ethylsulphonylbenzoic acid (0.1 mole), 100 ml of acetone, 26 ml of water and 10 g of triethylamine (0.1 mole) are placed in a 500 ml flask fitted with an agitator, a thermometer, a condenser and a dropping funnel. When the acid has dissolved, the solution is cooled to 5° C. and 14 g of isobutyl chloroformate (0.102 mole) is added drop by drop. The reaction medium is agitated for 30 minutes between +5° and +10° C. then cooled to +5° C. again. 20 g of 1-(-2'-norbornyl)-2-aminomethyl pyrrolidine (0.103 mole) is added drop by drop, then the medium is reacted for 2 hours at room temperature. The solvents are evaporated under vacuum, and the viscous residue is dissolved in 200 ml of water and 50 ml of acetic acid. The solution is filtered, and the filtrate is made alkaline with 500 ml of soda lye. The product is crystallised in the refrigerator, filtered, washed with water, dried in an oven, then re-crystallised in 200 ml of methanol. The white crystals are filtered, washed with a little chilled methanol and dried in an oven at 50° C. 25 g (57%) of product is obtained, melting at 175° C.

EXAMPLE 13

N(-1-norbornyl-2-pyrrolidylmethyl)-2-methoxy-4-bromo-5-sulphamoyl benzamide 2-methoxy-4-bromo-5-chlorosulphonyl-benzoic acid 300 ml of chlorosulphonic acid of density 1.766 (4.55 mole) is placed in a 1 liter flask fitted with an agitator, a thermometer and a condenser, and 69.3 g of 2-methoxy-4-bromobenzoic acid (0.30 mole) is added in stages. The reaction is slightly exothermic and the temperature reaches 40° C. by the time all the benzoic acid has been added. The reaction medium is heated to 80° C. then returned to room temperature. The solution, which is brown, is poured slowly over 2 kg of crushed ice.

The precipitate formed is filtered, washed with water and dried in an oven at 50° C. for 4 hours. 94 g of product is obtained, melting at 194° C.

2-methoxy-4-bromo-5-sulphamoyl-benzoic acid 1,290 ml of 22° Bé. ammonia is placed in a 3 liter flask fitted with an agitator and a thermometer. It is cooled, and 805 g of 2-methoxy-4-bromo-5-chlorosulphonyl-benzoic acid is added in stages between 0° and +10° C. The reaction medium is agitated for 1 hour at about +10° C. then the solution is filtered with charcoal. The filtrate is diluted with 300 ml of water and the acid precipitated by adding hydrochloric acid (density 1.18). The precipitate is drained, washed with water and dried in an oven at 50° C. 645 g (85%) of product is obtained, melting at 256° C.

2-methoxy-4-bromo-5-sulphamoyl-benzoyl chloride 183 ml of thionyl chloride (density 1.64), 61 g of 2-methoxy-4-bromo-5-benzoic acid (0.197 mole) and 2 drops of dimethylformamide are placed in a 500 ml flask fitted with an agitator, a condenser and a thermometer and are gradually heated to reflux. The reflux is maintained for 2 hours, then the excess $SOCl_2$ is expelled by distillation under vacuum. The residue is dissolved in 100 ml of toluene which is then expelled under vacuum. The product is dissolved in 180 ml of hexane, drained, washed with 40 ml of hexane and dried in an oven for 2 hours.

62 g (96%) of product is obtained; this decomposes at 185° C.

N-(1-norbornyl-2-pyrrolidylmethyl)-2-methoxy-4-bromo-5-sulphamoyl-benzamide 65 g of 1-norbornyl-2-amino-methyl-pyrrolidine (0.335 mole) and 500 ml of methyl-ethyl-ketone are placed in a 3 liter flask fitted with an agitator, a thermometer and a dropping funnel. The solution is cooled to +5° C., then a filtered solution of 109 g of 2-methoxy-4-bromo-5-sulphamoyl-benzoyl chloride in 2,000 ml of methyl-ethylketone is poured in drop by drop. The reaction medium is allowed to return to room temperature then left for 24 hours. The precipitate formed is filtered, washed with water and dried in an oven at 60° C. 146 g of product is obtained, with a melting point of over 250° C. This is suspended in 4 liters of boiling water, 200 ml of ammonia is added and the suspension is agitated for 1 hour at 80° C. It is cooled to 40° C. and filtered. The white crystals are washed with water then re-suspended in 200 ml of water. 100 ml of acetic acid is added, the solution obtained is filtered with charcoal and the base precipitated by adding 350 ml of ammonia. The crystals are drained, washed with water and dried in an oven at 60° C. 115 g (71%) of amide is obtained, melting at 202° C.

EXAMPLE 14

N-(1-cycloheptyl-2-pyrrolidinylmethyl)-2-methoxy-4-chloro-5-ethylsulphonyl-benzamide 39 g of 1-cycloheptyl-2-aminomethylpyrrolidine (0.200 mole) and 150 ml of methyl-ethyl-ketone are placed in a 1 liter flask fitted with an agitator, a thermometer, a condenser and a dropping funnel. The solution is cooled to +10° C., then 55 g of 2-methoxy-4-chloro-5-ethyl-sulphonyl-benzoyl chloride is added in stages. The reaction medium is agitated for 8 hours at room temperature then left to stand.

The precipitate is filtered, washed with a little ethanol and dried in an oven. Yield 78 g (85.5%). Melting point—160°-170° C. with decomposition.

The hydrochloride is dissolved hot in 500 ml of water. The solution is filtered in the presence of 3S black, then the filtrate is rendered alkaline with 60 ml of soda lye. An oil is precipitated. After 2 days in an ice chamber the crystaals formed are filtered, washed with water and dried in an oven at 40° C. 52.5 g of product is obtained and is dissolved in 200 ml of water and 7 g of acetic acid. The solution is diluted to 10% and filtered in the presence of carbon black. The product is re-precipitated by rendering the solution alkaline with 130 ml of 1N soda. The oil is crystallised, then the crystals are filtered, washed with water and dried in an oven. The product is re-crystallised in 100 ml of isopropanol. 43 g (51%) of product is obtained, with a melting point of 110° C.

EXAMPLE 15

N-(1-cyclohexyl-methyl-3-pyrrolidinyl)-2-methoxy-4-amino-5-chlorobenzamide 8 g of 2-methoxy-4-amino-5-chlorobenzoic acid (0.040 mole), 50 ml of acetone and 4 g of triethylamine (0.040 mole) are placed in a 250 ml flask fitted with an agitator, a thermometer and a dropping funnel. The suspension is cooled and 5.5 g of isobutyl chloroformate (0.040 mole) is added drop by drop between 0° and +5° C. The reaction medium is agitated for 45 minutes with the temperature kept between 0° and +5° C., then 8 g of 1-cyclohexyl-methyl-3-aminopyrrolidine (0.044 mole) is added drop by drop. The reaction is allowed to continue for 2 hours at room temperature, then 80 ml of water is added and the acetone is expelled. The product crystallises in the residual water. It is filtered and re-dissolved in 150 ml of water and 5 ml of concentrated hydrochloric acid. The solution is filtered with charcoal and the filtrate is made alkaline with 10 ml of ammonia (density 0.91). The viscous precipitate is decanted and dissolved in 80 ml of water and 5 ml of hydrochloric acid. The product is dissolved and the hydrochloride is precipitated very rapidly. It is drained, washed with water and dried at 50° C. 10.4 g of product is obtained and is dissolved hot in 100 ml of water. The solution is rendered alkaline with 10 ml of soda lye. The oily precipitate is crystallised by cooling. It is drained, washed with water and dried in an oven at 50° C.

The product is re-crystallised in 50 ml of diethylcarbonate. 7.7 g (53%) of product is obtained. Melting point about 110° C.

EXAMPLE 16

N-(1-cyclopropylmethyl-3-pyrrolidyl)-2-methoxy-4-bromo-5-methyl-sulphonyl-benzamide 2-methoxy-4-bromo-5-methylsulphonyl benzoic acid 66 g of sodium sulphite, 80 g of sodium bicarbonate and 280 ml of water are placed in a flask fitted with an agitator, a thermometer, a condenser and a dropping funnel. The mixture is heated to 60° C., then 92.4 g of 2-methoxy-4-bromo-5-chlorosulphonyl benzoic acid is added in stages.

When the reaction medium has been heated to 60°-70° C. for 3 hours 60 g of sodium bicarbonate is added then 106 g of dimethylsulphate is introduced slowly. The mixture is heated to reflux then cooled and acidified with hydrochloric acid. The precipitate formed is drained and dried in an oven at 50° C., then poured into 250 ml of boiling water. The suspension formed is agitated at boiling point, filtered hot, then the crystals are dried in an oven at 50° C. 34 g of 2-methoxy-4-bromo-5-methylsulphonyl benzoic acid is obtained (melting point 225°-258° C. Yield=39.3%).

N-(1cyclopropylmethyl-3-pyrrolidinyl)-2-methoxy-4-bromo-5-methylsulphonyl-benzamide 9.3 g of 2-methoxy-4-bromo-5-methylsulphonyl benzoic acid (0.030 mole), 70 ml of acetone, 10 ml of water and 4.2 ml of triethylamine of density 0.72 (0.030 mole) are placed in a 250 ml flask fitted with an agitator, a thermometer and a dropping funnel. A solution is obtained and cooled to about 0° C. 4.2 g of isobutyl chloroformate (0.030 mole) is added drop by drop, the reaction medium is agitated for 30 minutes with the temperature between 0° and +5° C., then 4.7 g of 1-cyclopropylmethyl-3-aminopyrrolidine (0.033 mole) is poured in drop by drop. The reaction is continued for 2 hours at room temperature then 50 ml of water and 5 ml of soda lye are added. The acetone is evaporated under vacuum and the oil, which is insoluble in water, is extracted twice, each time with 50 ml of methylene chloride. The organic solution is dried over magnesium sulphate and filtered, and the filtrate is evaporated under vacuum. The viscous residue is dissolved hot in 90 ml of isopropanol. The solution is acidified with 7 ml of 6N hydrochloric ethanol. The hydrochloride is crystallised in the refrigerator, then the crystals are filtered, washed with a little isopropanol and dried in an oven at 50° C.

The product is dissolved in 400 ml of tepid water and the solution is filtered, then rendered alkaline with 5 ml of soda lye. The base is precipitated in the form of an oil. The aqueous phase is decanted and the residue is dissolved hot in 100 ml of methylisobutylketone. It is crystallised in a refrigerator. The product is filtered, washed with a little methylisobutylketone then with water and dried in an oven at 50° C. 5.4 g (42%) of product is obtained, with a melting point of 147° C.

EXAMPLE 17

N-[1-(cyclohexenyl)-methyl-2-pyrrolidylmethyl]-2,3-dimethoxy-5-sulphamoyl-benzamide 13 g of 2,3-dimethoxy-5-sulphamoyl-benzoic acid (0.05 mole), 150 ml of acetone, 35 ml of water and 5 g of triethylamine (0.05 mole) are placed in a 500 ml flask fitted with an agitator, a thermometer, a condenser and a droping funnel. The mixture is cooled to between 0° to +5° C. and 5.5 g of ethyl chloroformate (0.05 mole) is poured in drop by drop. The reaction medium is agitated until the precipitate is completely dissolved, then re-cooled to 0° C. and 9.7 g of 1-(1-cyclohexenyl)-methyl-2-aminomethyl-pyrrolidine (0.05 mole) is poured in drop by drop.

The medium is reacted for 5 hours at room temperature then left to stand. The solvents are evaporated under vacuum and the residue is dissolved in 150 ml of hydrochloric acid (density 1.18). An insoluble oil is decanted off, then the aqueous solution is made alkaline with 13 ml of ammonia (density 0.91). The precipitate formed is filtered, washed with water and re-crystallised in 120 ml of isopropanol. 6.1 g of product is obtained and is re-crystallised in 250 ml of isopropanol. Yield=4.5 g (21%). M.P.=169° C.

EXAMPLE 18

N-(1-cyclohexyl-2-pyrrolidyl-methyl)-2-propargyloxy-3,5-dichlorobenzamide

Methyl 2-propargyloxy-3,5-dichlorobenzoate

A 5 liter flask fitted with a sealed agitator, a condenser and a thermometer is used. 320 g of methyl 3,5-dichlorosalicylate (1.45 mole), 1,280 ml of methyl-ethyl-ketone and 177 g of propargyl bromide (1.45 mole+3% excess) are placed in it, then 200 g of potassium carbonate (1.45 mole) and 21.5 g of sodium iodide (0.145 mole). A thick pulp is obtained, which becomes fluid when brought to reflux. The reflux is maintained for 8 hours.

Part of the methyl-ethyl-ketone is distilled, then the residue is dissolved in 2.8 liter of water in order to dissolve the mineral salts.

The precipitate is drained, washed with water until neutral and dried in air. 372 g (99%) of ester is obtained, melting at 78° to 79° C.

2-propargyloxy-3,5-dichloro-benzoic acid 372 g of methyl 2-propargyloxy-3,5 dichlorobenzoate (1.45 mole) is dissolved hot in 720 ml of ethanol (95°) in a 2 liter flask fitted with a reflux condenser. 145 ml of 30% soda lye (1.45 mole) is added and the solution is heated to reflux for 1 hour 30. With the reflux still maintained, 1 liter of water is added to finish the reaction. The solution is cooled, poured into 6.2 liters of water then filtered with charcoal. The acid is precipitated by adding 170 ml of concentrated hydrochloric acid. The white precipitate is drained, washed with water then dried in an oven at 60° C.

340 g of 2-propargyloxy-3,5-dichloro-benzoic acid is obtained. Yield 95.5%. M.P.=163°-164° C.

2-propargyloxy-3,5-dichloro-benzoyl chloride 86 g of 2-propargyloxy-3,5-dichlorobenzoic acid (0.35 mole) is reacted.

83.5 g of thionyl chloride (2×0.35 mole) is placed in a 500 ml flask fitted with a reflux condenser, followed by about half the organic acid, and the resultant suspension is heated gently in a water bath. Within an hour everything is dissolved. The solution is cooled and the second portion of acid is added. The mixture is heated until everything has dissolved, which takes 45 minutes.

The excess thionyl chloride is distilled under vacuum to constant weight. The remaining acid chloride crystallises. Weight obtained: 90 g. Yield: 97%. M.P.: 63°-64° C.

N-(1-cyclohexyl-2-pyrrolidyl-methyl)-2-propargyloxy-3,5-dichlorobenzamide 64 g of 1-cyclohexyl-2-aminomethyl-pyrrolidine (0.35 mole) is dissolved in 190 ml of chloroform in a 500 ml flask fitted with an agitator and a thermometer. The solution is cooled to +5° C., then 92 g of finely powdered 2-propargyloxy-3,5-dichlorobenzoyl chloride (0.35 mole) is gradually added in the course of about an hour, with the temperature kept between +5° and +10° C. The acid chloride gradually dissolves as this is added. The temperature is then raised to finish the reaction. The reaction mixture is dissolved in 1 liter of water then the chloroform is distilled. The aqueous solution which is left is filtered with charcoal, and the base is precipitated by adding 20% ammonia. It crystallises slowly. It is drained, washed with water and dried in an oven at 40° C. 137 g of product is obtained, melting at 79°-80° C.

The 137 g of base is re-crystallised in 275 ml of isopropanol. Weight obtained: 106 g of product. M.P.: 84°-85° C.

The product is purified by dissolving it in 1.5 liter of water and 29 ml of concentrated hydrochloric acid, filtering the solution with charcoal then adding 20% ammonia. The base crystallises slowly. It is drained, washed with water until the Cl⁻ ions are eliminated, then dried in an oven at 40° C.

104 g of N-(1-cyclohexyl-2-pyrrolidinyl-methyl)-2-propargyloxy-3,5-dichloro-benzamide is obtained. This is a white substance which melts at 84° to 85° C.

EXAMPLE 19

N(1-(1'adamantyl)-2-pyrrolidyl-methyl)-2-methoxy-5-sulphamoyl benzamide 55 g of 1-(1'adamantyl)-2-amino-methyl-pyrrolidine (0.235 mole), 300 ml of methyl-ethyl-ketone and 100 ml of water are placed in a 2 liter flask fitted with an agitator, a thermometer, a condenser and a dropping funnel.

A filtered solution of 58 g of 2-methoxy-5-sulphamoyl-benzoyl chloride (0.23 mole) in 700 ml of methyl-ethyl-ketone is poured in drop by drop while the temperature is kept at about 20° C.

The reaction medium is agitated for 1 hour then filtered. The crystals are washed with water and dried in an oven at 50° C. 60 g of product is obtained, melting between 250°-270° C.

It is dissolved in 1 liter of water containing 80 ml of glacial acetic acid. A light insoluble component is filtered off and the product is precipitated by adding ammonia to pH=8-9.

52 g of product is obtained, with a melting point of 245° C. After re-crystallisation in 700 ml of methyl acetoacetate then in dioxan an acid-base passing, 28 g of product is obtained with a melting point of 250° C.

EXAMPLE 20

N(1-(1'-adamantyl)-2-pyrrolidinyl-methyl)-2-methoxy-5-methyl-sulphonyl benzamide 46 g of 1-(1'-adamantyl)-2-amino-methyl-pyrrolidine (0.2 mole), 300 ml of methyl-ethyl-ketone and 50 ml of water are placed in a 1 liter flask fitted with an agitator, a thermometer and a condenser, then 41 g of 2-methoxy-4-methyl-sulphonyl-benzoyl chloride (0.16 mole) is added in stages.

The medium is reacted for 2 hours at 20° C., then the solution is evaporated under vacuum. 300 ml of water and 30 ml of 40% soda lye are added on the residue. The supernatant solution is decanted off and the viscous substance dissolved in 500 ml of boiling ethanol. The product is filtered and crystallised by chilling.

The product is filtered and re-crystallised twice running in 500 ml of ethanol. 35 g (49%) of white crystals is obtained, with a melting point of 174° C.

EXAMPLE 21

N(1-(1'-adamantyl)-2-pyrrolidinyl-methyl)-2-methoxy-4,5-azimido benzamide 56.5 g of methyl 2-methoxy-4,5-azimido-benzoate (0.27 mole) in 400 ml of butanol containing 70 g of 1-(1'-adamantyl)-2-amino-methyl-pyrrolidine (0.3 mole) is fed at 80° C. into a 1 liter flask fitted with a thermometer, and left to react for 60 hours in an oven at 70° C.

A light insoluble substance is filtered off hot and the filtrate is cooled and evaporated dry. The residue is dissolved hot in 600 ml of water and 60 ml of hydrochloric acid (density 1.18). The solution is filtered with carbon black then put in an ice chamber. The hydrochloride precipitate is filtered and dried in an oven. 87 g of product is obtained. This is dissolved in 800 ml of hot water then filtered with charcoal, and the base is precipitated by adding 195 ml of 1N soda. It is cooled and 500 ml of chloroform is added. The mixture is filtered, washed with water then with a little chloroform and isopropanol and dried in an oven at 50° C.

53 g of base is obtained and is dissolved hot in 500 ml of water and 20 ml of concentrated hydrochloric acid. The hydrochloride is precipitated by cooling. It is filtered off, washed with water and dried in an oven at 50° C. 48 g is obtained and is re-dissolved in 500 ml of hot water. 107 ml of 1N soda is added. The mixture is cooled, 500 ml of chloroform is added and the white precipitate is filtered off. This is washed with water then with a little isopropanol. 40 g of product is obtained. The hydrochloride-base passing is repeated to give 31.5 g (28.6%) of base with a melting point of 251° C.

EXAMPLE 22

N(1-(1'-adamantyl)-2-pyrrolidinyl-methyl))-2-methoxy-5-ethyl-sulphonyl-benzamide 70 g of 1-(1'-adamantyl)-2-aminomethylpyrrolidine (0.3 mole), 400 ml of methyl-ethyl-ketone and 150 ml of water are placed in a 1 liter flask fitted with an agitator and a thermometer.

78 g of 2-methoxy-5-ethylsulphonylbenzoyl chloride is added to the solution in stages. The reaction is exothermic and the temperature rises to 40° C. The medium is reacted for 3 hours then evaporated to dryness, and the residue is dissolved in 500 ml of methylene chloride. The organic solution is washed with 200 ml of 10% soda then dried over magnesium sulphate. It is filtered then the methylene chloride is evaporated. The viscous residue is dissolved in 500 ml of boiling methanol. The product is crystallised by cooling, filtered and re-crystallised a second time in 400 ml of methanol.

51.5 g (37.7%) is obtained with a melting point of about 103° C.

EXAMPLE 23

N-(1-cyclopentyl-2-pyrrolidinyl-methyl)-2-methoxy-5-sulphamoyl-benzamide 23 g of methyl 2-methoxy-5-sulphamoyl benzoate (0.09 mole) is dissolved hot, at about 90° C., in 115 ml of glycol in a 500 ml flask fitted with an agitator and a thermometer. The solution is cooled to 50° C. and the ester re-crystallises. 19 g of 1-cyclopentyl-2-amino-methyl-pyrrolidine is added. The suspension obtained is kept at 50° C. After 30 hours the ester is completely dissolved. The solution continues to be heated until a sample taken is found to be completely soluble in acetic acid. The solution is then cooled and the benzamide crystallises slowly. 150 ml of water is added and the precipitate is drained, washed with water and dried. 23 g (68%) of benzamide is obtained with a melting point of 147°-148° C. Since the benzamide hydrochloride is relatively insoluble in water, the benzamide is purified by dissolving the base at boiling point in water and HCl then filtering the solution obtained with 1 g of charcoal.

The hydrochloride is precipitated when cooled. It is drained, washed with 25 ml of cold water and dried. 21 g (84%) of hydrochloride is obtained with a melting point of 237°-238° C. The hydrochloride is dissolved in 150 ml of hot water, the solution is filtered with 3 g of charcoal and 6 ml of NH$_4$OH is added. The base is precipitated, initially in a viscous state, then solidifies. It is drained, washed with water and dried. 18 g of white crystals is obtained with a melting point of 156°-157° C. Total yield 53%.

EXAMPLE 4

N-(1-cyclohexyl-2-pyrrolidinyl-methyl)-2-methoxy-5-sulphamoyl-benzamide 118 g of ethyl 2-methoxy-5-sulphamoyl-benzoate, 41 ml of water and 100 g of 1-cyclohexyl-2-amino methyl-pyrrolidine are placed in a 500 ml flask fitted with a condenser. The suspension obtained is heated in a water bath at 90°-95° C. The ester dissolves gradually and after 2 hours 30 solubilisation is almost complete; the base formed then crystallises. Heating is continued until a sample taken is found to be totally soluble in dilute acids. The product obtained is dissolved in dilute acetic acid, the solution is filtered with charcoal, then the base is precipitated with 20% ammonia. The precipitate is initially in a viscous state, then solidifies. It is drained, washed with water until neutral and dried at 45° C. 152.5 g (85%) of product is obtained with a melting point from 191°-193° C.

148.5 g of base is suspended in 1,200 ml of water, 33 ml of hydrochloric acid (density 1.18) is added and the medium is heated to reflux until complete solubilisation is obtained. The solution is filtered with charcoal. The hydrochloride crystallises rapidly on cooling. It is drained, washed with 150 ml of iced water then dried in an oven at 45° C.

150 g of hydrochloride is collected, with a melting point of 245°-250° C.

It is re-dissolved hot in 1,200 ml of water, the solution is filtered with charcoal, then the base is precipitated by adding 40 ml of 20% ammonia. The base is initially in a liquid state, then solidifies. It is drained, washed with water and dried at 50° C.; the product is white and contains Cl$^-$ ions.

The following treatment is therefore applied:

119 g of base is dissolved in 480 ml of water and the necessary acetic acid. The solution obtained is filtered with charcoal then the base is re-precipitated by adding 20% ammonia. It is drained, washed with water and dried at 45° C.

111 g of N-(1-cyclohexyl-2-pyrrolidinyl-methyl)-2-methoxy-5-sulphamoyl-benzamide is obtained, with a melting point of 194°–195° C. Total yield 70%.

I.R. spectrum analysis shows that the product is a mixture of 2 polymorphic forms.

EXAMPLE 25

N-(1-cyclohexyl-2-pyrrolidinyl-methyl)-2-methoxy-4-amino-5-ethylsulphonyl-benzamide Using a 1 liter flask fitted with an agitator, a thermometer and a dropping funnel, 98 g of 2-methoxy-4-amino-5-ethylsulphonyl-benzoic acid (0.378 mole) is dissolved in 392 ml of acetone, then 38 g of triethyl amine (0.378 mole) is added. The triethyl amine salt of the organic acid crystallises immediately.

The suspension is cooled to 0° C. then 41 g of ethyl chlorofomate (0.378 mole) is added drop by drop between 0° and 5° C. The salt is dissolved gradually and the triethylamine hydrochloride is precipitated in fine white crystals.

Once the introduction stage is over the medium is agitated for ½ hour at 5° C., then 72 g of 1-cyclohexyl-2-amino-methyl-pyrrolidine is added drop by drop while the temperature is kept between 5° and 10° C. Agitation is continued for 1 hour with a rise in temperature. The suspension is cooled, then the triethylamine hydrochloride is drained and washed with acetone.

The filtrate is distilled under vacuum to constant weight. The residue obtained is dissolved in 800 ml of water and 35 ml of concentrated hydrochloric acid. The solution is filtered with charcoal then made alkaline with 40 ml of 20% ammonia. The base is precipitated in the form of oil, which is decanted off and extracted with methylene chloride. The organic solution obtained is washed several times with water and dried over potassium carbonate. The methylene chloride is then evaporated under vacuum to constant weight. The residue of 151 g is dissolved in 300 ml of hot isopropyl alcohol. The base is crystallised by cooling. It is drained, washed with isopropanol and dried at 45°. 125 g of product is obtained, melting at 162°–163° C. It is re-dissolved in 1 liter of water and 38 ml of concentrated hydrochloric acid. The solution obtained is filtered with charcoal then made alkaline by adding 20% ammonia. The base precipitated is initially viscous then crystallises. It is drained, washed with water and dried in an oven at 50° C.

123 g is obtained. The base contains a little water. It is crystallised in 355 ml of methanol. 100 g of N-(1-cyclohexyl-2-pyrrolidinyl-methyl)-2-methoxy-4-amino-5-ethylsulphonyl benzamide is collected.

EXAMPLE 26

N-(1-cyclohexylmethyl-2-pyrrolidinyl-methyl)-2,3-dimethoxy-5-sulphamoyl benzamide 26.1 g of 2,3-dimethoxy-5-sulphamoyl-benzoic acid (0.10 mole), 40 ml of water, 200 ml of acetone and 10.1 g of triethylamine (0.10 mole) are placed in a 500 ml flask fitted with an agitator, a thermometer and a dropping funnel. The solution is cooled to between 0° and +5° C. and 10.9 g of ethyl chloroformate (0.10 mole) is added drop by drop. It is agitated for 1 hour 30 with the temperature kept at about +5° C., then 19.6 g of 1-cyclohexylmethyl-2-aminomethyl pyrrolidine (0.10 mole) is added drop by drop. A precipitate forms progressively as more and more is added. The reaction medium is then agitated at room temperature, after which it is left to stand. The crystals are filtered, washed three times with water then with 100 ml of 10% ammonia and dried in an oven at 50° C. 50 g is obtained.

The product is dissolved in 300 ml of water and 10 ml of acetic acid, the solution is filtered and the filtrate is rendered alkaline with 20 ml of ammonia (density 0.91). It is crystallised in a refrigerator, filtered, washed with water and dried in an oven at 50° C. 28.5 g of product is obtained. Yield: 65%. M.P.: 189° C.

EXAMPLE 27

N-(1-cyclohexyl-2-pyrrolidinyl-methyl)-2,3-dimethoxy-5-methylsulphamoyl benzamide 125.5 g of methyl 2,3-dimethoxy-5-methylsulphamoyl benzoate (0.434 mole) and 500 ml of ethylene glycol are placed in a 1 liter flask, heated to 90° to dissolve everything, then cooled to 50° C. 95 g of 1-cyclohexyl-2-aminomethylpyrrolidine is added. The reaction mixture is kept at 50° C. for 106 hours. In the course of the reaction the base which forms is precipitated. The suspension is dissolved in 1.7 liters of water and 52 ml of concentrated hydrochloric acid (density 1.18). The solution obtained is filtered with charcoal and the base is precipitated with 60 ml of 20% ammonia. It is liquid at first, then solidifies. It is drained, washed with water and dried at 40° C. 176.5 g of product is collected, with a melting point of 161°–162° C.

The base is suspended in 2 liters of boiling water, after which a solution of 43 g of 85% phosphoric acid and 200 ml of water is added. The resultant solution is filtered with charcoal then chilled. The phosphate which crystallises is drained, washed with 200 ml of iced water and dried at 45°. 151 g of white product is obtained.

The phosphate is dissolved hot in 1,800 ml of water and the base is precipitated by 42 ml of soda lye. The suspension is cooled and filtered. The precipitate is washed in water and dried at 45° C.

121 g of benzamide is obtained, melting at 162°–163° C. Yield: 64%.

EXAMPLE 28

N-(1-cyclohexyl-2-pyrrolidinylmethyl)2,3-dimethoxy-5-methylsulphamoyl benzamide 55 g of 2,3-dimethoxy-5-methylsulphamoyl benzoic acid, 300 ml of tetrahydrofuran and 20.2 g of triethylamine are placed in a 1 liter flask fitted with an agitator, a thermometer and a dropping funnel. The suspension is agitated for 30 minutes then cooled. 27.3 g of isobutyl chloroformate is dripped in between 0° and +5° C. then left to react for 45 minutes at the same temperature. 40 g of 1-cyclohexyl-2-amino-methyl-pyrrolidine is next added drop by drop, between 0° and 5° C., agitated at that temperature for 30 minutes then for 2 hours at room temperature. It is left to stand, then the precipitate is filtered off, washed with 100 ml of chilled tetrahydrofuran and dried in an oven at 40° C. The 91 g of product obtained is suspended in 500 ml of boiling water, which is agitated for 1 hour. The product is filtered off hot and dried in an oven at 60° C.

60 g of product is obtained. This is dissolved in 290 ml of 0.5N hydrochloric acid and filtered with acticarbone 3S.

The filtrate is made alkaline with 20% ammonia. The precipitate is drained, washed with water then re-dissolved hot in 420 ml of 90% ethanol. It is re-crystallised in a refrigerator, filtered, washed with water and dried in an oven at 50° C.

55 g of product is obtained, melting at 166° C. Yield: 63%.

EXAMPLE 29

N-(1-cyclohexyl-2-pyrrolidinylmethyl)-2-methoxy-5-methylsulphamoyl-benzamide 123 g of ethyl 2-methoxy-5-methylsulphamoyl benzoate, 40 ml of water and 98 g of 1-cyclohexyl-2-aminomethyl-pyrrolidine are placed in a 500 ml flask fitted with a reflux condenser. The suspension is heated in a water bath at 90°–95° C. In 10 minutes the ester is completely dissolved. Heating is continued for 8 hours. The reaction medium is cooled and the base crystallises. It is re-dissolved in 800 ml of water and the necessary acetic acid. The solution is filtered with charcoal and the base is precipitated by adding 20% ammonia, with ether present to encourage crystallisation.

The precipitate is drained, washed with water, and dried in an oven at 45° C. 153 g of product is obtained, melting at 142°–145° C.

The base is re-crystallised, with filtration through charcoal, in 310 ml of absolute ethanol. 118 g is obtained, with a melting point of 149°–151° C.

A second re-crystallisation is carried out in 240 ml of absolute ethanol with filtration through charcoal. The N-(1-cyclohexyl-2-pyrrolidinyl methyl)2-methoxy-5-methyl-sulphamoyl-benzamide is obtained in the form of yellowish white crystals which melt 149°–151° C. Yield=57%.

The infra-red spectrum shows the product obtained to be a mixture of 2 crystalline forms.

EXAMPLE 30

N-(1-cyclopropyl-2-pyrrolidinyl methyl)-2-methoxy-5-methyl sulfinyl benzamide 53.5 g of 2-methoxy-5-methyl sulfinyl benzoic acid, 740 ml of acetone, 140 ml of water and 35 ml of triethylamine (density 0.726) are placed in a 2 liter flask fitted with an agitator, a thermometer and a dropping funnel. The solution is cooled to between 0° and +5° C., after which 34.1 g of isobutyl chloroformate is dripped in. The mixture is agitated for 45 minutes at 20° C. then cooled to 0° C., and 42 g of 1-cyclopropyl-2-amino methyl pyrrolidine is poured in drop by drop. The mixture is reacted at room temperature then left to stand. The solvents are evaporated under vacuum. The oily residue is dissolved in 250 ml of water and 50 ml of hydrochloric acid (density 1.18) and extracted twice with 125 ml of methylene chloride. The aqueous phase is then made alkaline with 70 ml of soda lye. A yellow oil is salted out. It is extracted 3 times with 250 ml of methylene chloride and the organic phase is washed 3 times with 100 ml of water and dried over magnesium sulphate. The solution is filtered and the solvent evaporated. An oily residue is obtained. It is dissolved in 500 ml of ethanol and an equimolar quantity of citric acid is added. It is evaporated under vacuum and the residue is dissolved in 1,000 ml of boiling isopropanol then cooled. The supernatant solution is decanted off and the residual paste dissolved in 600 ml of water. The solution is filtered with charcoal then the filtrate is evaporated under vacuum.

A very hygroscopic crystallised residue is obtained. Melting point about 70° C. NMR spectrum compatible.

EXAMPLE 31

N-(1-cyclopentyl-2-pyrrolidinyl methyl)-2-methoxy-4-amino-5-sulphamoyl benzamide 104 g of methyl 2-methoxy-4-amino-5-sulphamoyl benzoate (0.40 mole), 100.8 g of 1-cyclopentyl-2-aminomethyl pyrrolidine (0.60 mole) and 36 g of water are placed in a 1 liter flask fitted with an agitator, a thermometer and a condenser. The mixture is heated to 90°–95° C., left to stand then heated again to 95° C., distilling off the methanol formed. A sample of the reaction medium taken at that stage is completely soluble in a dilute solution of acetic acid. 500 ml of water is added to the suspension, which is cooled and then filtered. The precipitate is washed with water, re-suspended in 500 ml of water and acidified with 50 ml of acetic acid. The solution obtained is filtered in the presence of carbon black and the filtrate is made alkaline with 150 ml of ammonia. The precipitate is drained, washed with water and dried. 123 g of product is obtained, melting at 225° C. It is re-crystallised twice in a solution of 600 ml of dimethyl formamide and 210 ml of water.

93 g of product is obtained, containing a little solvent. The crystals are re-dissolved in 500 ml of water and 30 ml of acetic acid and are filtered with charcoal. The base is precipitated by adding 100 ml of ammonia to the filtrate. The white precipitate is drained, washed with water and dried in an oven at 60° C.

80 g of amide is obtained, melting at 232° C. Yield 50.5%.

EXAMPLE 32

N-(1-cyclohexyl-2-pyrrolidinylmethyl)-2-methoxy-4-amino-5-methylsulphamoyl benzamide 58.5 g of 2-methoxy-4-amino-5-methylsulphamoyl benzoic acid and 585 ml of acetone are placed in a 2 liter flask fitted with an agitator, a thermometer and a dropping funnel. The mixture is agitated and 22.7 g of triethylamine is added. A rubbery precipitate forms which then crystallises slowly. After being agitated for 45 minutes the suspension is cooled to 0° C. and 24.4 g of ethyl chloroformate is added drop by drop between 0° and 5° C. This is agitated for 45 minutes between 0° and 5° C., then 45.5 g of 1-cyclohexyl-2-aminomethyl-pyrrolidine is dripped in. The medium is reacted cold for 30 minutes then left to stand at room temperature. The triethylamine hydrochloride precipitate is filtered off and washed with 100 ml of acetone. The organic solution is evaporated to dryness under vacuum. The residue is dissolved in 500 ml of water and 50 ml of concentrated hydrochloric acid. The aqueous phase is extracted with 250 ml of methylene chloride, which is expelled. The aqueous phase is made alkaline with 70 ml of soda lye and the suspension is extracted twice with 250 ml of methylene chloride. The organic phase is washed twice with 250 ml of water, dried over magnesium sulphate then evaporated to dryness under vacuum. The residue is dissolved in 400 ml of isopropanol, 100 ml of hydrochloric isopropanol ($\frac{7}{8}$5N) is added and the hydrochloride is crystallised in a refrigerator. The precipitate is drained, made into a paste with 300 ml of acetone and dried in an oven at 50° C.

76 g is obtained (M.P. about 200° with decomposition).

The product is re-crystallised in 500 ml of ethanol. It is placed in an ice chamber for 3 days, then the white crystals are drained, washed twice with 60 ml of iced ethanol and dried in an oven at 30° then at 60° C.

64 g of hydrochloride is obtained. This melts at about 208° C. with decomposition.

EXAMPLE 33

N-(1-cyclohexyl methyl-2-pyrrolidinyl-methyl)-2-methoxy-4-amino-5-ethylsulphonyl-benzamide 25.9 g of 2-methoxy-4-amino-5-ethylsulphonyl benzoic acid, 40 ml of water, 200 ml of acetone and 13.9 ml of triethylamine (density 0.726) are placed in a 500 ml flask fitted with an agitator, a thermometer and a dropping funnel. The solution is cooled to about 0° to 5° C. and 10.9 g of ethyl chloroformate is dripped in. The mixture is agitated for 40 minutes at about 0° C., then 19.6 g of 1-cyclohexyl-methyl-2-aminomethyl pyrrolidine is added drop by drop. The mixture is agitated for 2 hours at room temperature then left to stand. The acetone is evaporated under vacuum and the residue is dissolved in 100 ml of water and 25 ml of acetic acid and filtered in the presence of vegetable black. The filtrate is made alkaline with 100 ml of 40% soda lye. A precipitate is formed; this is filtered, washed with plenty of water and dissolved moist in 230 ml of boiling acetone. The hot solution is filtered in the presence of vegetable black and the filtrate is crystallised. The product is drained, washed with a little acetone and dried in an oven at 50° C.

25 g (57%) of product is collected: melting point 155° C.

EXAMPLE 34

N-(1-cyclohexyl-2-pyrrolidinyl methyl)-2-methoxy-4-amino-5-methylsulphinyl benzamide

2-methoxy-4-amino-5-methylthio benzoic acid 3,600 ml of methanol is placed in a 6 liter flask fitted with an agitator, a thermometer, a condenser and a dropping funnel, and 495 g of potash (84% in pellet form) is added in stages. The temperature reaches 60° C. and the potash is completely dissolved. 357 g of methyl 2-methoxy-4-amino-5-thiocyano benzoate is then added and 280 ml of methyl iodide (density 2.28) is poured in drop by drop while the temperature is kept between 55° and 60° C. The mixture is heated to reflux then cooled to 15° C. and the mineral salts are filtered off. The filtrate is evaporated to dryness under vacuum. The solid residue is dissolved in 1,500 ml of water; the solution is filtered in the presence of vegetable black, after which the filtrate is acidified to pH 2-3 with hydrochloric acid. The precipitate which appears is drained, washed with water and dried in an oven at 50° C. Yield: 260 g (81%). M.P.: 143° C.

2-methoxy-4-acetamino-5-methyl-thio-benzoic acid 260 g of 2-methoxy-4-amino-5-methyl-thio-benzoic acid and 520 ml of acetic acid are placed in a 2 liter flask fitted with an agitator, a thermometer, a condenser and a dropping funnel. 123 ml of acetic anhydride (density 1.082) is poured in slowly. The temperature rises to reach 40° C. The reaction mixture is heated for 1 hour 30 at 85° C., cooled and poured over 1,000 g of ice and 1,000 ml of water. The precipitate which forms is filtered, washed with water and dried in an oven at 50° C.

278 g (89%) of product is obtained, melting at 165° C.

2-methoxy-4-acetamino-5-methyl-sulphinyl-benzoic acid 127.5 g of 2-methoxy-4-acetamino-5-methyl thio-benzoic acid and 200 ml of acetic acid are placed in a 500 ml flask fitted with an agitator, a thermometer, a condenser and a dropping funnel. A solution of 50 ml of 110 vol. hydrogen peroxide in 100 ml of acetic acid is poured drop by drop onto the suspension obtained. The reaction is exothermic. The temperature is kept between 20° and 30° C. by cooling. 30 minutes after the introduction stage is over the solution is clear. It is kept at from 25°-30° C. for a further 2 hours, the solvent is evaporated to dryness under vacuum, and the viscous residue is dissolved in 250 ml of acetone. The crystals formed are filtered, washed with a little acetone and dried in an oven at 50° C.

110 g (81%) of product is obtained, melting at 196° C.

N-(1-cyclohexyl-2-pyrrolidinyl-methyl)-2-methoxy-4-amino-5-methyl-sulphinyl-benzamide 81.3 g of 2-methoxy-4-acetamino-5-methylsulphinyl-benzoic acid (0.30 mole), 600 ml of acetone, 120 ml of water and 41.7 ml of triethylamine with a density of 0.726 (0.30 mole) are placed in a 1 liter flask fitted with an agitator, a thermometer, a condenser and a dropping funnel. The mixture is cooled to 0° C. and 40.8 g of isobutyl chloroformate (0.30 mole) is poured in drop by drop. It is agitated for 30 minutes with the cooling bath removed, cooled to 0° C. again and 54.6 g of 1-cyclohexyl-2-aminomethyl-pyrrolidine (0.30 mole) is poured in drop by drop. The mixture is reacted for 1 hour at room temperature with agitation, and left to stand. The solution is evaporated to dryness. A paste is obtained and is dissolved in 200 ml of soda and 400 ml of water. It is heated to reflux for 2 hours, and 50 ml of a mixture distilling over at low temperature is distilled off then put back under reflux. The reaction medium is left to stand, then the suspension is extracted four times with 200 ml of methylene chloride. The organic phase is washed twice with 300 ml of 10% hydrochloric acid, the aqueous phase is filtered with carbon black and the filtrate is made alkaline with 300 ml of 40% soda. The suspension is extracted 3 times, each time with 300 ml of methylene chloride. The organic solution is washed with water and dried over magnesium sulphate. The solution is filtered and evaporated to dryness. 42.5 g (36%) of benzamide is obtained; this does not crystallise.

The product is solubilised in 150 ml of isopropanol, and a solution of 22.7 g of citric acid, $H_2O$ in 200 ml of isopropanol is added hot. This is evaporated to dryness, dissolved in 500 ml of water and filtered in the presence of 3S carbon black, and the filtrate is evaporated to dryness under vacuum.

50.3 g (29%) of product is obtained, melting at about 125° C.

The NMR and IR spectra are compatible with the structure of the product.

EXAMPLE 35

N-(1-cyclopentyl-2-pyrrolidinyl methyl)-2-methoxy-4-amino-5-ethyl-sulphinyl benzamide 2-methoxy-4-acetamino-5-ethylsulphinyl benzoic acid 123.7 g of 2-methoxy-4-acetamino-5-ethyl thiobenzoic acid and 184 ml of acetic acid are placed in a 1 liter flask fitted with an agitator, a thermometer, a condenser and a dropping funnel. A solution of 46.5 ml of 110 vol. hydrogen peroxide in 103 ml of acetic acid is poured in drop by drop. The reaction is exothermic and the temperature is kept at about 30° C. The product is completely dissolved, then a white precipitate appears. Agitation is continued for 1 hour, after which the suspension is cooled to 10°. The precipitate is drained, washed with acetic acid and dried in an oven at 50° C.

90 g of product is obtained, melting at 199° C. (yield 69%).

N-(1-cyclopentyl-2-pyrrolidinyl-methyl)-2-methoxy-4-amino-5-ethylsulphinyl benzamide 85.5 g of 2-methoxy-4-acetamino-5-ethylsulphinyl benzoic acid, 85 ml of water, 342 ml of acetone and 31 g of triethylamine are placed in a 1 liter flask fitted with an agitator, a thermometer and a dropping funnel. The mixture is agitated until the solids dissolve, then 32.5 g of ethyl chloroformate is added drop by drop while the temperature is kept at about 10° C. The reaction medium is agitated for 30 minutes at room temperature then cooled to 5°–10° C. and 50.4 g of 1-cyclopentyl-2-aminomethylpyrrolidine is added drop by drop in the course of 1 hour. Agitation is continued for 2 hours at room temperature, then the reaction mixture is evaporated to dryness under vacuum. The residue is dissolved in 300 ml of water and the suspension is extracted with 500 ml then twice with 300 ml of methylene chloride. The organic phase is washed twice with 200 ml of water and evaporated under vacuum. The oily residue is dissolved hot in 300 ml of water. 90 ml of soda lye is added and the medium is heated to reflux for 2 hours 30. An oil appears rapidly. It is cooled, the suspension is extracted twice with 250 ml methylene chloride, and the organic solution is washed three times with 200 ml of water. It is dried over magnesium sulphate, filtered and evaporated to dryness under vacuum. The residue is dissolved in 320 ml of ethyl acetate, then the product is left to crystallise in a refrigerator. The crystals are filtered off and dried in an oven at 50° C.

65 g of product is obtained (melting point 168° C.). It is re-crystallised in 200 ml of isopropanol and 10 ml of water. The solution is chilled for 24 hours, then the crystals are filtered off and dried.

33 g of product is obtained, melting at 183° C. (yield 28%).

EXAMPLE 36

N-(1-cyclopentyl-2-pyrrolidinyl methyl)-2,4-dimethoxy-5-ethylsulphonyl benzamide 2,4-dimethoxy-5-chlorosulphonyl benzoic acid 1,800 ml of chlorosulphonic acid is placed in a 4 liter flask fitted with an agitator and a thermometer, and is cooled to 10° C. 328 g of finely powdered 2,4-dimethoxy benzoic acid is added in stages in the course of 45 minutes, between 10° and 15° C. The acid dissolves gradually as it is introduced. When all the acid has been added the solution is gradually heated to 55° C. and that temperature is maintained for 5 hours. The solution is left to stand overnight, then poured little by little into 17 kg of ice, with agitation and with external cooling. The acid which is precipitated is drained, washed with water and dried in air.

456 g is obtained. Yield 90%.

2,4-dimethoxy-5-mercaptobenzoic acid 145 g of 2,4-dimethoxy-5-chlorosulphonyl benzoic acid, 393 ml of acetic acid and 230.5 g of tin are placed in a 6 liter flask fitted with an agitator, a thermometer and a dropping funnel, and the thick suspension is heated to 40° C. 1,009 ml of hydrochloric acid (density 1.18) is added drop by drop while cooling so as to keep the temperature at from 40° to 45°. The reaction is exothermic. The suspension dissolves gradually, the more acid is added, but the tin salts are precipitated about midway through the adding process. When all the acid has been added the water bath is heated to 55°–60° until the tin has dissolved. 2 liters of water is added and the acid which has precipitated is drained and washed with 460 ml of 10% hydrochloric acid, then with water. It is immediately re-dissolved in water and the necessary soda, the solution is filtered with charcoal, and the acid is re-precipitated by adding concentrated hydrochloric acid. The precipitate is drained, washed with water and dried in an oven at 40°.

86.5 g is obtained. Yield 78%.

2,4-dimethoxy-5-ethyl thiobenzoic acid

In a 2 liter flask fitted with a reflux condenser, 173 g of 2,4-dimethoxy-5-mercapto benzoic acid is dissolved in 525 ml of water and 162 ml of soda lye, and 135 g of ethyl sulphate is added. The solution obtained is heated to reflux. It is cooled, then ethylation is recommenced with 40.5 ml of soda lye and 76 g of ethyl sulphate, and the medium is heated in the same way till it has very low alkalinity.

40 ml of soda lye is added and the medium is heated for ½ hour under reflux. The solution is then diluted with 1.4 liter of water and filtered through charcoal.

The acid is precipitated by adding hydrochloric acid, drained and washed with water. It is immediately re-dissolved in water and sodium carbonate, the solution is filtered with charcoal to eliminate an insoluble substance, and the acid is re-precipitated by adding concentrated hydrochloric acid. It is drained, washed with water and dried in an oven at 40°.

144 g (74%) of product is obtained, with a melting point from 94° to 96° C.

2,4-dimethoxy-5-ethylsulphonyl benzoic acid 124 g of 2,4-dimethoxy-5-ethyl thiobenzoic acid and 765 ml of acetic acid are placed in a 3 liter flask fitted with a reflux condenser and are heated gently to dissolve all the solids. 306 ml of 112 volume hydrogen peroxide is added; the solution immediately becomes clear. It is boiled gently for 3 hours and finally heated for 1 hour with the naked flame in order to destroy the excess hydrogen peroxide.

The 2,4-dimethoxy-5-ethylsulphonyl benzoic acid is crystallised by cooling. It is drained, washed with 120 ml of acetic acid then water and dried at 40° C.

99 g of product is collected with a melting point of 207°–208° C. Yield 70%.

2,4-dimethoxy-5-ethylsulphonyl benzoyl chloride 82.2 g of 2,3-dimethoxy-5-ethylsulphonyl benzoic acid, 165 ml of thionyl chloride and 3 drops of D.M.F. are placed in a 500 ml flask fitted with an agitator, a reflux condenser and a thermometer.

The suspension is heated slowly to reflux. After 1 hour 30 the temperature is stabilised at 78°–79° C. Heating is continued for another 2 hours, after which the solution is cooled slightly and the excess thionyl chloride expelled by distillation under vacuum. The solid residue is dissolved in 125 ml of isopropyl ether and the crystals are filtered off. They are washed with 125 ml of isopropyl ether, dried for 1 hour in an oven at 45°–50° C., then kept in a desiccator under vacuum.

86 g of acid chloride (98%) is obtained, with a melting point of 186° C.

N-(1-cyclopentyl-2-pyrrolidinyl methyl)-2,4-dimethoxy-5-ethyl sulphonyl-benzamide 33.6 g of 1-cyclopentyl-2-amino-methyl pyrrolidine and 200 ml of methyl-ethyl-ketone are placed in a liter flask fitted with an agitator, a thermometer and a condenser. The solution is cooled, then 58.5 g of 2,4-dimethoxy-5-ethylsulphonyl benzoyl chloride (0.2 mole) is added in stages over about 45 minutes, while the temperature is kept between 0° and +5° C. The solution obtained is kept at +5° C. for 30 minutes and at room temperature for 2 hours 30. A precipitate forms after 1 hour's agitation at room temperature. The hydrochloride crystals are filtered, washed with 50 ml of methyl-ethyl-ketone and dried in an oven at 50°–60° C.

82 g of hydrochloride is obtained, M.P. 186° C.

The product is dissolved in 400 ml of water and filtered in the presence of charcoal. The filtrate is made alkaline with 25 ml of soda lye diluted with 75 ml of water. The precipitate crystallises rapidly. It is drained, washed with water and dried in an oven at 50°–60° C.

69 g of product is obtained, with a melting point of 113° C.

The base is re-crystallised in 210 ml of 90% ethanol. The crystals are chilled overnight, drained and washed with 70 ml of 90° ethanol then twice with 100 ml of water. They are dried in an oven at 50° C.

62 g (73%) of benzamide is obtained with a melting point of 162° C.

EXAMPLE 37

N-(1-cycloheptyl-2-pyrrolidinyl methyl)-2-methoxy-5-methyl sulphonyl-benzamide 52 g of 1-cycloheptyl-2-amino-methyl-pyrrolidine and 240 ml of water are placed in a 500 ml flask fitted with an agitator, a condenser and a thermometer. They are cooled to 0°, then 62.1 g of 2-methoxy-5-methyl sulphonyl-benzoyl chloride (0.250 mole) is added in stages while the temperature is kept at from 0° to +5° C. The temperature is raised; at about 20° an exothermic reaction commences and the temperature rises to 30° C. After 1 hour's agitation everything is dissolved. The reaction is continued for a further 30 minutes, then the solution is filtered in the presence of acticarbone 3S. The filtrate is made alkaline with 20 ml of soda lye diluted with 80 ml of water. The precipitate is initially rubbery, then crystallises. It is drained, washed with water and dried in an oven at 50° C.

90.5 g is obtained, with a melting point from 112° to 114° C.

The base is re-crystallised twice, respectively in 225 ml and 200 ml of methanol containing 30% of water. The white crystals are drained and dried in an oven at 40° C.

54 g of product is obtained with a melting point of 118° C. Yield 53%.

EXAMPLE 38

N-(1-cycloheptyl-methyl-2-pyrrolidinyl methyl)-2-methoxy-4-amino-5-methyl-sulphamoyl benzamide 6.5 g of 2-methoxy-4-amino-5-methyl sulphamoyl benzoic acid, 75 ml of acetone, 14 ml of water and 3.5 ml of triethylamine (density 0.726) are placed in a 250 ml flask fitted with an agitator, a thermometer, a condenser and a dropping funnel. The solution is cooled to between 0° and +5° C. and 2.7 g of ethyl chloroformate is added drop by drop. The reaction medium is agitated for 45 minutes at room temperature then cooled to 0° C. again. 6.8 g of 1-cycloheptyl methyl-2-amino methyl pyrrolidine is added drop by drop. The medium is reacted for 2 hours then left to stand. The solvents are expelled and the solid residue dissolved in 50 ml of water and 20 ml of hydrochloric acid (density 1.18). The suspension obtained is made alkaline with ammonia. It is extracted 3 times with 50 ml of methylene chloride. The organic phase is washed twice with 50 ml of water, dried over magnesium sulphate and filtered. The filtrate is evaporated to dryness under vacuum. The residue is dissolved in 80 ml of water and 20 ml of hydrochloric acid (density 1.18). The hydrochloride crystallises. It is drained, washed with water and dried in an oven at 50° C.

7 g of product is obtained, with a melting point of about 230° C.

It is re-crystallised in 300 ml of ethanol.

4.3 g (35%) of benzamide hydrochloride is obtained, with a melting point of 228° C.

EXAMPLE 39

N-(1-cycloheptyl methyl-2-pyrrolidinyl methyl)-2-methoxy-4-amino-5-ethyl sulphonyl benzamide 4.9 g of 2-methoxy-4-amino-5-ethyl sulphonyl benzoic acid, 57 ml of acetone, 10 ml of water and 2.6 ml of triethylamine (density 0.726) are placed in a 250 ml flask fitted with an agitator, a thermometer, a condenser and a dropping funnel. The solution is cooled to between 0° and +5° C. and 2.1 g of ethyl chloroformate is added drop by drop. The reaction medium is agitated for 45 minutes at room temperature then cooled to 0° C. and 5.3 g of 1-cycloheptyl methyl-2-amino methyl pyrrolidine is added in drop by drop. The medium is agitated for 4 hours then left to stand overnight. The solvents are evaporated to dryness and the residue is dissolved in 60 ml of water and 15 ml of hydrochloric acid (density 1.18). Extraction is carried out 3 times with 50 ml of methylene chloride, the organic phase is dried over magnesium sulphate and filtered, and the solvent is evaporated under vacuum. The residue is dissolved in 100 ml of water. The solution is filtered in the presence of carbon black and the filtrate is made alkaline with about 7 ml of ammonia (density 0.91). A gum is precipitated. It is extracted 3 times with 50 ml of methylene chloride. The organic phase is washed twice with 50 ml of water, dried over magnesium sulphate and filtered.

The solvent is evaporated under vacuum and the residue is re-crystallised in 100 ml of isopropanol.

4.5 g (52%) of product is obtained, with a melting point of 156° C.

EXAMPLE 40

N-(1-cyclopropylmethyl-2-pyrrolidinyl methyl)-2,4-dimethoxy-5-methyl-sulphonyl benzamide 2,4-dimethoxy-5-methylsulphonyl benzoic acid 930 ml of water, 208 g of sodium sulphite and 277 g of sodium bicarbonate are placed in a 6 liter flask fitted with a sealed agitator, a reflux condenser and a thermometer. They are heated to 70°–80° and 309 g of 2,4-dimethoxy-5-chlorosulphonyl benzoic acid is added gradually.

A large amount of $CO_2$ is given off simultaneously with the dissolving of the acid. The acid takes 45 minutes to introduce. Heating is continued for a further 2 hours at 70°–80° to complete the reaction. The pH of the solution is about 7.

220 cc of 30% soda lye, 1,120 ml of absolute alcohol and 470 g of methyl iodide are added to the reaction mixture and it is heated with a gentle reflux. After 3 hours 30 a weight loss of 50 g is noted and the solution is found to be only very slightly alkaline with phenolphthalein.

50 g of methyl iodide and 110 cc of soda lye are added and the medium is heated to reflux again. The initial reflux temperature rises progressively to 65° then to 75°. Another weight loss is observed but the solution remains alkaline. Heating is continued for 8 hours altogether.

500 ml of alcohol is then distilled off. The residue is dissolved in 2 liters of water and the mineral salts dissolved. The solution obtained, which is slightly turbid, is filtered with charcoal. The 2,4-dimethoxy-5-methylsulphonyl benzoic acid is precipitated by adding concentrated hydrochloric acid until it turns Congo red. It is drained, washed with water and dried at 60° C.

255 g of product is obtained (89%).

2,4-dimethoxy-5-methyl-sulphonyl-benzoyl chloride 161 g of 2,4-dimethoxy-5-methyl sulphonyl-benzoic acid is reacted. 590 g of thionyl chloride, 5 drops of dimethylformamide and about half of the organic acid are placed in a 2 liter flask filtered with a reflux condenser. The resultant suspension is heated in a water bath at 55° for about 5 minutes. The second half of the organic acid is added and heating is continued for 20 minutes at 60°–65° then for 45 minutes at 70°–75°. The medium becomes fluid and turns yellow. The acid dissolves gradually, while the acid chloride begins to crystallise. When the reaction is over the excess thionyl chloride is distilled to constant weight, finishing up under vacuum.

169 g (98%) of acid chloride is obtained. This melts with decomposition at 200° C.

N-(1-cyclopropyl methyl-2-pyrrolidinyl methyl)-2,4-dimethoxy-5-methyl sulphonyl benzamide.

74 g of 1-cyclopropylmethyl-2-aminomethyl-pyrrolidine and 460 ml of chloroform are placed in a liter flask fitted with an agitator and a thermometer. 134 g of finely powdered 2,4-dimethoxy-5-methylsulphonyl benzoyl chloride is added gradually. The temperature is kept between 5° and 10° by cooling in an iced bath. Each portion of acid chloride dissolves immediately. It takes 1 hour to introduce. Agitation is then continued for 1 hour at 5° then for 1 hour at room temperature.

The solution obtained is dissolved in 1 liter of water and the chloroform is distilled off. This leaves in suspension a light percipitate which is drained, washed and dried. 6 g of 2,4-dimethoxy-5-methylsulphonyl benzoic acid is recovered in this way (M.P. 208°–310°).

The aqueous solution is then made alkaline by adding 20% ammonia until it turns phenolphthalein. Ether is present to aid in crystallising the base. The product is drained, washed with water and dried at 45° C.

153 g (81%) of product is obtained, with a melting point of 193°–196° C.

After re-crystallising in 900 ml of acetonitrile, 133 g of benzamide is collected, with a melting point of 190°–191° C. Total yield 70%.

EXAMPLE 41

N-(1-cyclo octylmethyl-2-pyrroliinylmethyl)-2,3-dimethoxy-5-sulphamoyl benzamide 13 g of 2,3-dimethoxy-5-sulphamoyl benzoic acid, 130 ml of acetone, 28 ml of water and 7 ml of triethylamine (density 0.726) are placed in a 250 ml flask fitted with an agitator, a thermometer, a condenser and a dropping funnel. The resultant suspension is cooled to 0° C., then 5.4 g of ethyl chloroformate is poured in drop by drop and allowed to react at room temperature. It is then cooled to 0° C. again and 13.8 g of 1-cyclooctyl-2-aminomethyl-pyrrolidine is added drop by drop. The reaction medium is brought back to room temperature and left to stand.

The solvents are evaporated under vacuum and the residue is dissolved in 100 ml of water and 20 ml of hydrochloric acid (density 1.18). The solution is extracted 3 times with 25 ml of methylene chloride. 3 phases are formed. The aqueous solution and intermediate phase are made alkaline with 25 ml of ammonia (density 0.91). A gum is precipitated and crystallises slowly. The product is filtered, washed with water and dried in an oven at 40° C. It is re-crystallised in 100 ml of isopropanol. The product is filtered, washed with a little isopropanol and dried at 50° C.

Yield 8.6 g (38%). M.P. 164° C.

EXAMPLE 42

N-(1-cycloheptylmethyl-2-pyrrolidinylmethyl)-2,3-dimethoxy-5-sulphamoyl benzamide 13 g of 2,3-dimethoxy-5-sulphamoyl benzoic acid, 150 ml of acetone, 28 ml of water and 7 ml of triethylamine (density 0.726) are placed in a 250 ml flask fitted with an agitator, a thermometer, a condenser and a dropping funnel. The resultant solution is cooled from 0° to +5° C. 5.4 g of ethyl chloroformate is added drop by drop and the reaction medium is agitated for 45 minutes at room temperature and cooled to 0° C. again. 13.7 g of 1-cycloheptylmethyl-2-aminomethylpyrrolidine is added drop by drop. The medium is agitated for 1 hour at room temperature then left to stand. The crystals formed are drained, washed with water and dried in an oven at 30° C.

Yield 22.3 g (98%). M.P. 180° C.

The product is re-crystallised in 400 ml of isopropanol.

14.3 g (63%) of amide is collected, melting at 180° C.

EXAMPLE 43

N-(1-cyclopropylmethyl-3-pyrrolidinyl)-2-methoxy-5-sulphamoyl-benzamide 30 g of 1-cyclopropylmethyl-3-amino-pyrrolidine and 300 ml of water are placed in a liter flask fitted with an agitator, a thermometer and a condenser. The mixture is cooled to about 10° C. and 50 g of 2-methoxy-5-sulphamoyl benzoyl chloride is added in stages. The temperature of the resultant suspension is raised to about 20° C. then it is heated for 1 hour at 30° C. The solution obtained is filtered with charcoal then made alkaline with 20% ammonia. A rubbery precipitate forms and crystallises shortly afterwards. The crystals are filtered, washed with water and dried in an oven at 50° C. 66 g of product with a melting point of 142° C. is obtained.

The product is re-crystallised in 400 ml of ethanol.

45 g of N-(1-cyclopropylmethyl-3-pyrrolidinyl)-2-methoxy-5-sulphamoyl-benzamide is obtained: melting point 150° C. Yield 64%.

EXAMPLE 44

N-(1-cyclohexylmethyl-3-pyrrolidinyl)-2-methoxy-5-methylsulphonyl benzamide.

36.4 g of 1-cyclohexylmethyl-3-amino-pyrrolidine and 200 ml of water are placed in a 500 ml flask fitted with an agitator and a thermometer. The solution is cooled to +5° C., then 47.7 g of 2-methoxy-5-methylsulphonyl benzoyl chloride is added in stages. The suspension is then agitated for 2 hours at 20° C. followed by 1 hour at 30° C. The reaction medium is left to stand then strongly acidified with 30 ml of hydrochloric acid (density 1.18). A light insoluble substance is filtered off and the base is precipitated by making it alkaline with 60 ml of soda lye. The base is initially oily, then crystallises. The white crystals are filtered off, washed with water and dried in an oven at 50° C. 57.2 g of product is obtained, with a melting point of 152° C.

The product is re-crystallised with filtration in a hot state in 600 ml of methanol. It is left to re-crystallise overnight in a refrigerator. The crystals are filtered, washed with a little methanol and dried in an oven at 60° C.

51 g of N-(1-cyclohexylmethyl-3-pyrrolidinyl)-2-methoxy-5-methylsulphonyl-benzamide is obtained, with a melting point of 157° C. Yield 68%.

EXAMPLE 45

N-(1-cyclopropylmethyl-3-pyrrolidinyl)-2-methoxy-4-amino-5-methylsulphamoyl benzamide 7.8 g of 2-methoxy-4-amino-5-methylsulphamoyl benzoic acid, 70 ml of acetone, 10 ml of water and 3 g of triethylamine are placed in a 250 ml flask fitted with an agitator, a thermometer and a dropping funnel. The solution is cooled to about 0° C. and 4.3 g of isobutyl chloroformate is added drop by drop. It is agitated for 45 minutes at a temperature of from 0° to +5° C., after which 4.6 g of 1-cyclopropylmethyl-3-amino-pyrrolidine is added drop by drop. The medium is reacted for 2 hours at room temperature and 70 ml of water and 7 ml of soda lye is added. The acetone is evaporated under vacuum and the aqueous phase acidified with 10 ml of hydrochloric acid (density 1.18).

The aqueous phase is made alkaline with 15 ml of ammonia. A gum is precipitated. This is decanted then washed by decantation 3 times with 30 ml of water. The viscous residue is dissolved hot in 90 ml of isopropanol and 10 ml of water. The solution is filtered hot then put in a refrigerator to crystallise. The crystals are filtered, washed with water and dried in an oven at 50° C.

5.8 (50%) of product is obtained with a melting point of 177° C.

EXAMPLE 46

N-(1-cyclopropylmethyl-3-pyrrolidinyl)-2-methoxy-4-amino-5-ethyl-sulphonyl-benzamide 64.8 g of 2-methoxy-4-amino-5-ethylsulphonyl benzoic acid, 650 ml of acetone and 25.2 g of triethylamine are placed in a liter flask fitted with an agitator, a thermometer and a dropping funnel. The solids dissolve completely then the triethylamine salt is precipitated rapidly. The reaction medium is cooled to 0° C. and 35 g of isobutyl chloroformate is poured in drop by drop. The medium is agitated for 45 minutes between 0° and 5° C., after which 37 g of 1-cyclopropylmethyl-3-aminopyrrolidine is added drop by drop. The reaction is continued for 2 hours at room temperature, after which 500 ml of water is added and the acetone evaporated under vacuum. An oil is decanted and is extracted with methylene chloride. The organic phase is dried over magnesium sulphate, filtered and evaporated to dryness under vacuum. The residue is dissolved hot in 500 ml of diethylcarbonate and the product is put in an ice chamber to crystallise. The crystals are filtered, washed with a little ether and dried in an oven at 40°.

78 g of product is obtained with a melting point of 71°–72° C.

EXAMPLE 47

N-(1-cyclohexylmethyl-3-pyrrolidinyl)-2-methoxy-4-amino-5-ethyl-sulphonyl-benzamide 7.8 g of 2-methoxy-4-amino-5-ethylsulphonyl benzoic acid, 70 ml of acetone, 10 ml of water and 3 g of triethylamine are placed in a 250 ml flask fitted with an agitator, a thermometer and a dropping funnel. The mixture is cooled to 0° C. and 4.1 g of isobutyl chloroformate is poured in drop by drop. It is agitated for 45 minutes at 0° C. and 6 g of 1-cyclohexylmethyl-3-amino-pyrrolidine is dripped in. The reaction is continued for 2 hours at room temperature, 80 ml of water and 5 ml of soda lye are added, then the acetone is evaporated under vacuum. An oil is decanted; it is washed twice with 100 ml of water than dissolved hot in 50 ml ethyl acetate. It is chilled in a refrigerator. The crystals are filtered off, washed with a little ethyl acetate then dried in an oven at 50° C.

9.4 of benzamide is obtained with a melting point of 146° C. (74%).

EXAMPLE 48

N-(1-cyclohexylmethyl-3-pyrrolidinyl)-2-methoxy-4-amino-5-ethylsulphinyl benzamide 8.5 g of 2-methoxy-4-acetamino-5-ethylsulphinyl benzoic acid, 70 ml of acetone, 10 ml of water and 3 g of triethylamine are placed in a 250 ml flask fitted with an agitator, a thermometer and a dropping funnel. The solution is cooled to about 0° C., after which 4.2 g of isobutyl chloroformate is poured in drop by drop. It is agitated for 45 minutes at 0° C. then 6 g of 1-cyclohexylmethyl-3-amino-pyrrolidine is dripped in. It is reacted for 2 hours at room temperature, 50 ml of water is added and the acetone is evaporated under vacuum. 10 ml of soda and 50 ml of water are added to the aqueous residue and it is heated to reflux for 5 hours then cooled. The suspension is extracted twice with 50 ml of methylene chloride, and the organic phase is dried over magnesium sulphate and filtered. The filtrate is evaporated dry under vacuum, and the residue is dissolved in 70 ml of hot ethyl acetate. The product is re-crystallised by cooling and filtered. It is washed with a little ether and dried in an oven at 50° C.

8.2 g of product is obtained, with a melting point of 143° C. This is re-crystallised a second time in 90 ml of ethyl acetate. 6.8 g of amide is collected, with a melting point of 146° C.

EXAMPLE 49

N-(1-cyclopropylmethyl-3-pyrrolidinyl)-2-4-dimethoxy-5-ethylsulphonyl benzamide 8.2 g of 2,4-dimethoxy-5-ethylsulphonyl benzoic acid, 70 ml of acetone, 10 ml of water and 4.2 ml of triethylamine (density 0.726) are placed in a 250 ml flask fitted with an agitator, a thermometer and a dropping funnel. The solution obtained is cooled, then 4.2 g of isobutyl chloroformate is poured in drop by drop while the temperature is kept at about 0° C. The medium is reacted for 45 minutes at that temperature, after which 4.6 g of 1-cyclopropylmethyl-3-aminopyrrolidine is added drop by drop. It is agitated for 2 hours at normal temperature, then 50 ml of water and 5 ml of soda lye are added. The acetone is evaporated under vacuum and the insoluble oil extracted 3 times with 50 ml of methylene chloride. The organic phase is washed twice with 50 ml of water then dried over magnesium sulphate, filtered and evaporated to dryness. The oily residue is dissolved hot in 80 ml of butyl acetate. The solution is filtered then put in a refrigerator to crystallise. The crystals are drained, washed with a little ether and dried in an oven at 50° C.

8 g (67%) of product is obtained, with a melting point of 106° C.

EXAMPLE 50

N-(1-cyclopropylmethyl-3-pyrrolidinylmethyl)-2,3-dimethoxy-5-sulphamoyl benzamide 6.6 g of 2,3-dimethoxy-5-sulphamoyl benzoic acid, 50 ml of acetone, 10 ml of water and 3.6 ml of triethylamine (density 0.726) are placed in a 250 ml flask fitted with an agitator, a thermometer and a dropping funnel. The solution is cooled to 0°-+5° C. and 3.6 g of isobutyl chloroformate is poured in drop by drop. It is reacted for 30 minutes with the same temperature maintained, after which 4.8 g of 1-cyclopropylmethyl-3-aminomethyl-pyrrolidine is added drop by drop. The reaction medium is agitated for 1 hour at room temperature, whereupon 50 ml of water is added and the acetone evaporated under vacuum. A further 50 ml of water is added and the solution is made alkaline with 5 ml of ammonia (density=0.91). An oil is precipitated. The suspension is extracted 3 times with 50 ml of methylene chloride. The organic phase is dried over magnesium sulphate, filtered, then evaporated under vacuum. The residue is dissolved in boiling ethyl acetate. It crystallises hot. The crystals are cooled, filtered and dried in an oven at 50° C.

2.7 g (27%) of product is obtained, with a melting point of 146° C.

EXAMPLE 51

N-(1-cyclohexylmethyl-3-pyrrolidinyl)-2,3-dimethoxy-5-sulphamoyl benzamide 7.85 g of 2,3-dimethoxy-5-sulphamoyl benzoic acid, 50 ml of acetone, 10 ml of water and 3 g of triethylamine are placed in a 250 ml flask fitted with an agitator, a thermometer and a dropping funnel. The mixture is cooled to 0° and 4.2 g of isobutyl chloroformate is poured in drop by drop. The mixture is agitated for 45 minutes at 0° C., after which 6 g of 1-cyclohexylmethyl-3-amino-pyrrolidine is dripped in. It is agitated for 2 hours at room temperature, then 80 ml of water is added and the acetone evaporated under vacuum. The product crystallises. It is filtered, washed with water then re-dissolved in 150 ml of water and 20 ml of hydrochloric acid. The solution is filtered with charcoal and the filtrate made alkaline with ammonia. An oil is precipitated and crystallises slowly. The crystals are drained, washed with water and dried in an oven at 50° C. 6.8 g (53%) of product is obtained, with a melting point of 167° C.

EXAMPLE 52

N-(1-cyclopropylmethyl-3-pyrrolidinyl)-2-methoxy-5-ethylsulphonyl-benzamide 7.3 g of 2-methoxy-5-ethylsulphonyl benzoic acid, 70 ml of acetone, 10 ml of water and 4 g of triethylamine are placed in a 250 ml flask fitted with an agitator, a thermometer and a dropping funnel. The solution is cooled to about 0° C. and 4.2 g of isobutyl chloroformate is added drop by drop. The reaction medium is then agitated for 45 minutes between 0° and +5° C., after which 4.6 g of 1-cyclopropylmethyl-3-amino-pyrrolidine (0.033 mole) is poured in drop by drop. The medium is reacted for 2 hours.

50 ml of water and 5 ml of 40% soda lye are added, the acetone is evaporated under vacuum and the resultant suspension is extracted twice with 50 ml of methylene chloride. The organic phase is dried over magnesium sulphate and filtered and the solvent is evaporated under vacuum. The residual oil is dissolved in 80 ml of isopropanol. It is acidified with 7 ml of hydrochloric ethanol≃4.7N and left to stand in a refrigerator. The crystals are filtered off and dried in an oven at 50° C. The hydrochloride obtained melts at 170° C.

Yield 5.5 g (46%).

EXAMPLE 53

N-(1-cyclopropylmethyl-3-pyrrolidinyl methyl)-2-methoxy-5-sulphamoyl benzamide 5.8 g of 2-methoxy-5-sulphamoyl benzoic acid, 50 ml of acetone, 10 ml of water and 3.6 ml of triethylamine (density 0.726) are placed in a 250 ml flask fitted with an agitator, a thermometer and a dropping funnel. The solution is cooled to about +10° C., then 3.6 g of isobutyl chloroformate is added drop by drop. The medium is reacted for 30 minutes at 0° C., after which 4.5 g of 1-cyclopropylmethyl-2-aminomethyl-pyrrolidine is poured in drop by drop. The medium is reacted for 1 hour at room temperature, 50 ml of water is added and the acetone is evaporated under vacuum. The reaction medium is further diluted with 50 ml of water and made alkaline with 10 ml of ammonia (density 0.91). The viscous product which is precipitated crystallises slowly. The solid is filtered off, washed with water and re-crystallised in 50 ml of ethanol. 3.8 g 841%) of benzamide is obtained, melting at 177° C.

EXAMPLE 54

N-(1-cyclooctyl-2-pyrrolidinyl methyl)-2,4-dimethoxy-5-methyl-sulphonyl benzamide 13 g of 2,4-dimethoxy-5-methyl sulphonyl benzoic acid, 150 ml of acetone, 28 ml of water and 7 ml of triethylamine (density 0.726) are placed in a 250 ml flask fitted with an agitator, a thermometer, a condenser and a dropping funnel. The suspension is cooled to from 0° to +5° C., then 5.4 g of ethyl chloroformate is added drop by drop. The mixture is agitated for 45 minutes at room temperature and cooled to about 0° C., then 13.8 g of 1-cyclooctyl-2-aminomethyl-pyrrolidine is added drop by drop. There is complete solubilisation. The reaction medium is agitated at room temperature then left to stand. The solvents are evaporated under vacuum and the residue is dissolved in 100 ml of water and 20 ml of hydrochloric acid (density 1.18). The organic phase is extracted 3 times with 50 ml of methylene chloride, dried over magnesium sulphate, filtered and evaporated to dryness under vacuum. The residue is dissolved in 100 ml of water. The solution is filtered in the presence of carbon black and the filtrate made alkaline with 10 ml of ammonia. A gum is precipitated. This is extracted 3 times with 50 ml of methylene chloride, and the organic solution is washed twice with 50 ml of water and dried over magnesium sulphate. It is filtered, then the solvent is evaporated under vacuum and the residue re-crystallised in 200 ml of isopropanol. The crystals are filtered off, washed twice with a little iced isopropanol and dried in an oven at 50° C.

Yield 14.2 g (63%). The product melts at 158°–159° C.

EXAMPLE 55

N-(1-cyclopentyl-2-pyrrolidinyl methyl)-2,4-dimethoxy-5-methylsulphonyl benzamide 91 g of 2,4-dimethoxy-5-methylsulphonyl benzoic acid, 400 ml of acetone, 130 ml of water and 48.6 ml of triethylamine are placed in a liter flask fitted with an agitator, a thermometer and a dropping funnel. 47.6 g of isobutyl chloroformate is dripped into the solution obtained, at about 10° C. It is agitated for 40 minutes, then 58.8 g of 1-cyclopentyl-2-aminomethyl-pyrrolidine is poured in drop by drop at about 0° C. A precipitate appears after 30 minutes of agitation at room temperature. It is allowed to react then the precipitate is filtered off, washed with water and dried. 74 g of a crude version of the product is obtained, melting at 198° C.

The filtrate is evaporated to dryness under vacuum. The residue is dissolved in 200 ml of water and 20 ml of soda lye. The insoluble product is filtered off, washed with water and dried in an oven. This final version weighs 47 g.

The mixture of the first and second versions is dissolved in 1,300 ml of water containing 40 ml of hydrochloric acid (density 1.18). The solution is filtered in the presence of 5 g of charcoal and the product is re-precipitated by adding 45 ml of soda lye. A gum is formed and crystallises slowly. The product is filtered off, washed with water and dried in an oven at 60° C. 95 g of amide is obtained.

The crystals are dissolved in 2,500 ml of boiling acetonitrile. The solution is filtered and cooled in a refrigerator. The precipitate is drained, washed with a little acetonitrile then with water and dried in an oven at 50° C.

73 g (51%) of product is obtained, with a melting point of 212° C.

The products of the invention are used in the form of capsules, tablets, pills, in granulated form or as an injectable solution; the preparation of these is known per se. Substances which are inert relative to the compounds of the invention can be used, such as lactose, magnesium stearate, starch, talc, cellulose, levilite, alkali metal lauryl-sulphates, saccharose and the vehicles commonly employed in medicinal preparations.

The compounds may be administered in doses of 50–750 mg per day taken in 1 or more stages.

The examples which follow concern pharmaceutical preparations made in conventional manner from the compounds of the invention.

EXAMPLE 56 tablets

| | |
|---|---|
| N—(1-cyclopropylmethyl-2-pyrrolidinylmethyl) 2,3-dimethoxy-5-sulphamoyl benzamide | 100 mg |
| dried starch | 20 mg |
| lactose | 100 mg |
| methylcellulose 1500 cps | 1.5 mg |
| levilite | 10 mg |
| magnesium stearate | 4 mg | for 1 tablet.

EXAMPLE 57 capsules

| | |
|---|---|
| N—(1-cyclopropylmethyl-2-pyrrolidinylmethyl) 2-methoxy-4-amino-5-ethylsulphonyl benzamide | 50 mg |
| microcrystalline cellulose | 50 mg |
| methylcellulose 1500 cps | 1 mg |
| magnesium stearate | 5 mg |
| talc | 2 mg | for 1 capsule.

EXAMPLE 58 injectable solution

N-(1-cyclopropylmethyl-2-pyrrolidinylmethyl)

| | |
|---|---|
| N—(1-cyclopropylmethyl-2-pyrrolidinylmethyl) 2,3-dimethoxy-5-sulphamoyl benzamide | 40 mg |
| 1N hydrochloric acid | 0.10 ml |
| sodium chloride | 14 mg | for 2 ml

EXAMPLE 59 injectable solution

| | |
|---|---|
| N—(1-cyclopropylmethyl-2-pyrrolidinylmethyl) 2-methoxy-4-amino-5-ethylsulphonyl benzamide | 100 mg |
| 1N hydrochloric acid | 0.250 ml |
| sodium chloride | 8 mg | for 2 ml

To prepare the tablets, the selected compound is mixed with the starch and lactose by the method of successive dilutions; the mixture is granulated with methylcellulose. The levilite, magnesium stearate and talc are added to the granules before proceeding with compression.

It is possible to replace the methylcellulose with any other appropriate granulating agent, such as ethylcellulose, polyvinylpyrrolidone or starch paste. The magnesium stearate may be replaced by stearic acid.

When preparing injectable solutions, it is possible to dissolve the compound of the invention in the following acids: hydrochloric or levulinic acid, gluconic acid, or glucoheptonic acid.

The solution is prepared under sterile conditions and made isotonic with an alkali metal chloride such as sodium chloride, then preservatives are added. It is also possible to prepare the same solution without adding any preservatives: the ampoule is then filled under nitrogen and sterilised for ½ hour at 100° C.

The pharmacodynamic tests on the compounds of the invention, and particularly a study of their antiemetic power (antagonism to apomorphine administered subcutaneously to the dog is 5 to 20 times greater than that of known compounds of the same series) have show strong nervous system activity, as apomorphine antagonist.

Their low toxicity and the absence of any undesirable side-effects such as catalepsy, which normally accompany this type of product, make these compounds particularly important.

The acute toxicity of the compounds of the invention has been studied in the mouse. The lethal doses 50 are set out in the following table:

| LD$_{50}$ IN THE MALE MOUSE - EXPRESSED IN mg/kg | | | | |
|---|---|---|---|---|
| COMPOUND | I.V. | I.P. | S.C. | ORAL |
| 1 | 60–64,5 | 372–403 | 930 | 2280 |
| 2 | 52,5–54,6 | 203,5–220 | 380–396 | 1260–1325 |
| 3 | 152–155 | | 555 | |
| 4 | 48 | | 725 | |
| 5 | 48–52,5 | 264–280 | 924 | 3600–3630 |
| 6 | 51–51,75 | 96–108 | 170–186 | |
| 7 | 72–73,8 | 159,5–172 | 290–319 | 600–682 |
| 8 | 23,5–25,8 | 70–72,5 | 90–93 | 256 |
| 9 | 84–87,5 | 172,5–188,5 | 450 | 1020–1080 |
| 10 | 26,4–28,7 | 77,5–78 | 85–86 | 198–210 |
| 11 | 15,3–15,6 | 79,2–81,6 | 180–184 | 300–320 |
| 12 | 55,9–56,4 | 132–133 | 407–420 | 510–546 |
| 13 | 40,8–41 | | | |
| 14 | 31,2–32 | 82–87 | 128–138 | 259–270 |
| 15 | 28,8–29 | | | |
| 16 | 61,5–62 | 175–180 | 430–444 | 400–414 |
| 17 | 96–105 | 159,5–162 | | |
| 18 | 26,4–27 | 103–106 | 120–126 | 599–626 |
| 19 | 62,5–68,2 | 258–280 | 703 | |
| 20 | 64,5–70 | 221 | 590–614 | 514–516 |
| 21 | 41,8–45,6 | 147–152 | | |
| 22 | 37–40,8 | 133–145,2 | 336–342 | 348–380 |
| 23 | 51,8–52,8 | 185 | | 560–572 |

Compound 1  N—(1-cyclopropylmethyl-2-pyrrolidinylmethyl)-2,3-dimethoxy-5-sulphamoyl benzamide
Compound 2  N—(1-cyclopropylmethyl-2-pyrrolidinylmethyl)-2-methoxy 4-amino-5-ethylsulphonyl benzamide.
Compound 3  N—(1-cyclopropyl-2-pyrrolidinylmethyl)-2-methoxy-5-sulphamoyl benzamide.
Compound 4  N—(1-cyclopentyl-2-pyrrolidinylmethyl)-2-methoxy-5-sulphamoyl benzamide.
Compound 5  N—(1-cyclohexyl-2-pyrrolidinylmethyl)-2-methoxy-5-sulphamoyl benzamide
Compound 6  N—(1-cyclohexyl-2-pyrrolidinylmethyl)-2-methoxy-4-amino 5-ethylsulphonyl benzamide.
Compound 7  N—(1-cyclohexyl-2-pyrrolidinylmethyl)-2,3-dimethoxy-5-methylsulphamoyl benzamide
Compound 8  N—(1-cyclohexyl-2-pyrrolidinylmethyl)-2-methoxy-4-amino 5-chloro benzamide.
Compound 9  N—(1-cyclohexyl-2-pyrrolidinylmethyl)-2-methoxy-5-methylsulphamoyl benzamide -continued

| LD$_{50}$ IN THE MALE MOUSE - EXPRESSED IN mg/kg |
|---|
| Compound 10  N—(1-cyclohexyl-2-pyrrolidinylmethyl)-2-methoxy-4,5-azimido benzamide |
| Compound 11  N—(1-cyclohexyl-2-pyrrolidinylmethyl)2-propargyloxy-3,5-dichlorobenzamide |
| Compound 12  N—(1-(1'-adamantyl)-2-pyrrolidinylmethyl)-2-methoxy-5-methylsulphonyl benzamide. |
| Compound 13  N—(1-(1'-adamantyl)-2-pyrrolidinylmethyl)-2-methoxy-5-sulphamoyl benzamide. |
| Compound 14  N—(1-(1'-adamantyl)-2-pyrrolidinylmethyl)-2-methoxy-5-ethylsulphonyl benzamide |
| Compound 15  N—(1-(1'-adamantyl)-2-pyrrolidinylmethyl)-2-methoxy-4,5-azimido benzamide |
| Compound 16  N—(1-cycloheptyl-2-pyrrolidinylmethyl)-2-methoxy-5-methylsulphonyl benzamide |
| Compound 17  N—(1-cyclohexylmethyl-3-pyrrolidinyl)-2-methoxy-5-methylsulphonyl benzamide |
| Compound 18  N—(1-cyclohexyl-2-pyrrolidinylmethyl)-2-methoxy-4-amino-5-methylsulphamoyl benzamide |
| Compound 19  N—(1-cyclopropylmethyl-3-pyrrolidinyl)-2-methoxy-5-sulphamoyl benzamide. |
| Compound 20  N—(1-cyclopentyl 2-pyrrolidinylmethyl)-2-methoxy-4-chloro-5-ethylsulphonyl benzamide |
| Compound 21  N—(1-cyclopentyl-2-pyrrolidinylmethyl)-2-methoxy-4-amino 5-ethylsulphinyl benzamide. |
| Compound 22  N—(1-cyclohexylmethyl-2-pyrrolidinylmethyl)-2-methoxy-4-amino-5-ethylsulphonyl benzamide. |
| Compound 23  N—(1-(2'-norbornyl)-2-pyrrolidinylmethyl)-2-methoxy-4-amino-5-ethylsulphonyl benzamide. |

The antiemetic power relative to apomorphine has been measured on the dog by the method of Chen and Ensor.

The compounds of the invention were administered subcutaneously 30 minutes before the apomorphine, which was administered subcutaneously in a dose of 100 μg/kg.

The following results were obtained:

| ED$_{50}$ subcutaneously in the dog - expressed in μg/kg. | | | | | | | |
|---|---|---|---|---|---|---|---|
| COMPOUND | 1 | 2 | 3 | 12 | 16 | 17 | 22 |
| ED$_{50}$ | 2.2 | 0.4 | 8 | 9.5 | 2 | 1.75 | Effect of 89° at 10 μg/kg |

The compounds of the invention have virtually no cataleptic action.

The benzamides were administered subcutaneously to male rats. The criterion for the cataleptic state was that the animal should be immobile for 30 seconds with its rear limbs apart, arranged carefully on wooden cubes four cm high, thus putting the animal in an unaccustomed and uncomfortable position. The cataleptic action was measured when the effect was at its maximum, i.e. 5–6 hours after the product had been administered.

It was found that a dose of 100 mg/kg compounds 2, 5, 6, 9, 10, 13, 15, 18, 19, 20, 21 and 23 were completely free from any cataleptic action and that at a dose of 200 mg/kg compounds 1, 7, 12 and 14 produced a cataleptic state in 10% of the animals.

We claim:

1. Substituted heterocyclic benzamides, their salts of addition with pharmacologically acceptable acids, their quaternary ammonium salts, their N-oxides and their optically active isomers, of formula (I):

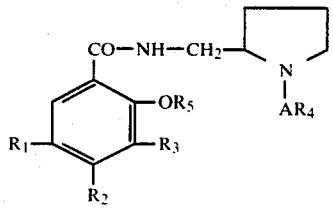 (I)

wherein:
A is a single bond
R$_4$ is a norbornyl or adamantyl group
R$_5$ is a C$_{1-3}$ alkyl group
R$_1$ is a sulfamoyl group or a, C$_{1-3}$ alkylsulfonyl group
R$_2$ is a hydrogen or halogen atom, an amino group or is joined with R$_1$ to form an azimido group
R$_3$ is a hydrogen atom.

2. The substituted heterocyclic benzamides of claim 1 wherein:
A is a single bond
R$_4$ is a norbornyl or adamantyl group
R$_5$ is a methyl group
R$_1$ is a sulfamoyl group or a, C$_{1-2}$ alkylsulfonyl group
R$_2$ is a hydrogen atom, an amino group or is joined with R$_1$ to form an azimido group
R$_3$ is a hydrogen atom.

3. N-(1-adamantyl 2-pyrrolidinylmethyl) 2-methoxy 5-methylsulfonyl benzamide.

4. N-(1-adamantyl 2-pyrrolidinylmethyl) 2-methoxy 5-ethylsulfonyl benzamide.

5. A pharmaceutical composition having anti-emetic activity which comprises the substituted heterocyclic benzamide of claim 1 or 2 and a pharmaceutically acceptable carrier.

6. A process for the treatment of nausea in patients which comprises administering an effective amount of the substituted heterocyclic benzamide of claim 1 or 2 and a pharmaceutically acceptable carrier.

7. N-(1-(2'-norbornyl)-2-pyrrolidinyl methyl) 2-methoxy-4-amino-5-ethylsulfonyl benzamide.

* * * * *

UNITED STATES PATENT AND TRADEMARK OFFICE
CERTIFICATE OF CORRECTION

PATENT NO. : 4,673,686
DATED : June 16, 1987
INVENTOR(S) : MICHEL THOMINET, ET AL.

It is certified that error appears in the above-identified patent and that said Letters Patent is hereby corrected as shown below: On the title page

AT [73] UNDER ASSIGNEE

Line 2,    "Industrielle" should read --Industrielles--.

AT [60] UNDER RELATED U.S. APPLICATION DATA

Line 4,    "505,191," should read --005,191,--.

AT [56] UNDER REFERENCES CITED/U.S. PATENT DOCUMENTS

Line 4,    "Podisva et al." should read --Podesva et al.--.
    Line 8,    "Berigi et al." should read --Beregi et al.--.
    Line 17,   "Halley, II et al." should read --Hadley et al.--.
    Line 18,   "Hatley et al." should read --Hadley et al.--.
    Line 22,   "Dosert et al." should read --Dostert et al.--.

AT [56] UNDER REFERENCES CITED/OTHER PUBLICATIONS

Line 3,    "Abst. C83" should read --Abst. (C83--.

COLUMN 1

Line 16,   "show" should read --shown--.

COLUMN 3

Line 55,   "above mentioned" should read --above-mentioned--.

COLUMN 5

Line 43,   "6liter" should read --6 liter--.

UNITED STATES PATENT AND TRADEMARK OFFICE
CERTIFICATE OF CORRECTION

PATENT NO. : 4,673,686
DATED : June 16, 1987
INVENTOR(S) : MICHEL THOMINET, ET AL.

It is certified that error appears in the above-identified patent and that said Letters Patent is hereby corrected as shown below:

COLUMN 6 line 30,   "79%." should read --79%.)--.

COLUMN 9

Line 59,   "dimmethylsulphamoyl" should read --dimethylsulphamoyl--.

COLUMN 10

Line 9,   "to" should read --at--.
    Line 16,   "≃→" should be deleted.
    Line 57,   "clear cut" should read --clear-cut--.

COLUMN 11

Line 5,   "clear cut" should read --clear-cut--.
    Line 43,   "b)" should be deleted.

COLUMN 12

Line 56,   "046732772" should be deleted.

COLUMN 13

Line 49,   "pyrrolidyl)methyl)" should read --pyrrolidylmethyl)--.

COLUMN 14

Line 40,   "5-benzoic" should read --5-sulphomoyl-benzoic--.
    Line 62,   "ethylketone" should read --ethyl-ketone--.

UNITED STATES PATENT AND TRADEMARK OFFICE
CERTIFICATE OF CORRECTION

PATENT NO. : 4,673,686  
DATED : June 16, 1987  
INVENTOR(S) : MICHEL THOMINET, ET AL.

Page 3 of 5

It is certified that error appears in the above-identified patent and that said Letters Patent is hereby corrected as shown below:

COLUMN 15

Line 28, "crystaals" should read --crystals--.

COLUMN 16

Line 28, "(1cyclopropylmethyl" should read --(1-cyclopropylmethyl--.

COLUMN 17

Line 3, "droping" should read --dropping--.  
    Line 35, "liter" should read --liters--.

COLUMN 20

Line 28, "$NH_4$ OH" should read --$NH_4OH$--.  
    Line 33, "EXAMPLE 4" should read --EXAMPLE 24--.

COLUMN 21

Line 22, "chlorofomate" should read --chloroformate--.

COLUMN 24

Line 63, "(7/85N)" should read --(≈5N)--.

COLUMN 31

Line 47, "filtered" should read --fitted--.

UNITED STATES PATENT AND TRADEMARK OFFICE
CERTIFICATE OF CORRECTION

PATENT NO. : 4,673,686
DATED : June 16, 1987
INVENTOR(S) : MICHEL THOMINET, ET AL.

It is certified that error appears in the above-identified patent and that said Letters Patent is hereby corrected as shown below:

COLUMN 32

Line 7, "(M.P. 208°-310°)." should read --(M.P. 208°-210°).--.
Line 21, "pyrroliinylmethyl)" should read --pyrrolidinylmethyl)--.

COLUMN 34

Line 51, "9.4" should read --9.4g (74%)--.
Line 52, "(74%)." should be deleted.

COLUMN 36

Line 20, "50°C. 6.8g" should read --50°C. ¶ 6.8g--.
Line 61, "2-aminomethyl" should read --3-aminomethyl--.

COLUMN 37

Line 1, "ethanol. 3.8g841%)" should read --ethanol. ¶ 3.8g(41%)--.

COLUMN 38

Line 46, "N-(1-cyclopropylmethyl-2-pyrrolidinylmethyl)" should be deleted.

COLUMN 39

Line 21, "show" should read --shown--.
Lines 35-54, In the Table every "," (comma) should be changed to a --.-- (decimal point).

UNITED STATES PATENT AND TRADEMARK OFFICE
CERTIFICATE OF CORRECTION

PATENT NO. : 4,673,686
DATED : June 16, 1987
INVENTOR(S) : MICHEL THOMINET, ET AL.

It is certified that error appears in the above-identified patent and that said Letters Patent is hereby corrected as shown below:

COLUMN 40

Line 6, "pyrrolidinylmethyl)2-" should read --pyrrolidinylmethyl-2- --.
Line 44, "89° at" should read --89% at--

COLUMN 41

Line 16, "a, $C_{1-3}$" should read --a $C_{1-3}$--.

COLUMN 42

Line 4, "a, $C_{1-2}$" should read --a $C_{1-2}$--.

Signed and Sealed this

Eighth Day of December, 1987

Attest:

DONALD J. QUIGG

Attesting Officer

Commissioner of Patents and Trademarks